(12) United States Patent
Shmelkov et al.

(10) Patent No.: US 7,396,680 B2
(45) Date of Patent: Jul. 8, 2008

(54) STEM CELL-SPECIFIC PROMOTERS AND THEIR USE

(75) Inventors: Sergey V. Shmelkov, New York, NY (US); Shahin Rafii, Great Neck, NY (US); Jun Lin, Forest Hills, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/974,265

(22) Filed: Oct. 27, 2004

(65) Prior Publication Data

US 2005/0125849 A1 Jun. 9, 2005

Related U.S. Application Data

(60) Provisional application No. 60/516,229, filed on Oct. 31, 2003.

(51) Int. Cl.
  C12N 15/00 (2006.01)
  C12N 5/02 (2006.01)
(52) U.S. Cl. .................. 435/320.1; 435/325
(58) Field of Classification Search .............. 435/320.1, 435/325
  See application file for complete search history.

(56) References Cited

OTHER PUBLICATIONS

Corbeil et al. J. Biol. Chem. 275(8):5512-5520; 2000.*
Yu et al. J. Biol. Chem. 2777(23):20711-20716; 2002.*
GenBank Accession No. AY275524.*
GenBank AC108063 pp. 1-63; Mar. 9, 2002.*
Miraglia et al., "A Novel Five-Transmembrane Hematopoietic Stem Cell Antigen: Isolation, Characterization, And Molecular Cloning," Blood, 90:5013-5021 (1997).
Yin et al., "AC133, A Novel Marker For Human Hematopoietic Stem And Progenitor Cells," Blood, 90:5002-5012 (1997).
Peichev et al., "Expression Of VEGFR-2 And AC133 By Circulating Human CD34+ Cells Identifies A Population Of Functional Endothelial Precursors," Blood, 95:952-958 (2000).
Salven et al., "VEGFR-3 And CD133 Identify A Population Of CD34+ Lymphatic/Vascular Endothelial Precursor Cells," Blood, 101:168-172 (2003).
Uchida et al., "Direct Isolation Of Human Central Nervous System Stem Cells," Proc. Natl Acad. Sci. USA, 97:14720-14725 (2000).
Lee et al., "Isolation Of Neural Stem Cells From The Postnatal Cerebellum," Nature Neuroscience, 8:723-729 (2000).
Richardson et al., "CD133, A Novel Marker For Human Prostatic Epithelial Stem Cells," J. Cell Sci., 117:3539-3545 (2004).
Singh et al., "Identification Of A Cancer Stem Cell In Human Brian Tumors," Cancer Research, 63:5821-5828 (2003).
Singh et al., "Identification Of Human Brain Tumour Initiating Cells," Nature, 432:396-401 (2004).
Rafii et al., "Therapeutic Stem And Progenitor Cell Transplantation For Organ Vascularization And Regeneration," Nature Medicine, 9:1-11 (2003).
Heissig et al., "Recruitment Of Stem And Progenitor Cells From The Bone Marrow Niche Requires MMP-9 Mediated Release of Kit-Ligand," Cell, 109:625-637 (2002).
Kim et al., "The Emerging Fields Of Suicide Gene Therapy And Virotherapy," Trends In Molecular Medicine, 8:68-73 (2002).
Yazawa et al., "Current Progress In Suicide Gene Therapy For Cancer," World Journal Of Surgery, 26:783-789 (2002).
Denny, "Prodrugs For Gene-Directed Enzyme-Prodrug Therapy (Suicide Gene Therapy)," Journal Of Biomedicine And Biotechnology, 2003:48-70 (2003).

* cited by examiner

*Primary Examiner*—Anne Marie S. Wehbe
*Assistant Examiner*—Fereydoun G. Sajjadi
(74) *Attorney, Agent, or Firm*—Nixon Peabody LLP

(57) ABSTRACT

The present invention relates to a method of isolating stem cells from a mixed population of different cell types. This method involves selecting a promoter which functions only in said stem cells and not in the other cell types. The promoter can have a nucleotide sequence selected from the group consisting of SEQ ID NO: 4, SEQ ID NO: 5, SEQ ID NO: 6, SEQ ID NO: 7, and SEQ ID NO: 8. A nucleic acid molecule encoding a marker protein under control of said promoter is introduced into all cell types of said mixed population and only the stem cells, but not the other cell types, within said mixed population are allowed to express said marker protein. The cells of said mixed population of cell types that are expressing the marker protein, which are restricted to the stem cells are identified and separated from the mixed population, where the separated cells are restricted to the stem cells. The promoter, nucleic acid constructs comprising it, and the resulting stem cells are also disclosed. The nucleic constructs can be incorporated in transgenic animals in order to monitor stem cell movement. A disorder mediated by stem cell proliferation can be carried out by administering both (1) a nucleic acid construct comprising the promoter of the present application and an enzyme capable of converting a prodrug to a cytotoxic drug and (2) the prodrug.

11 Claims, 7 Drawing Sheets

Figure 1
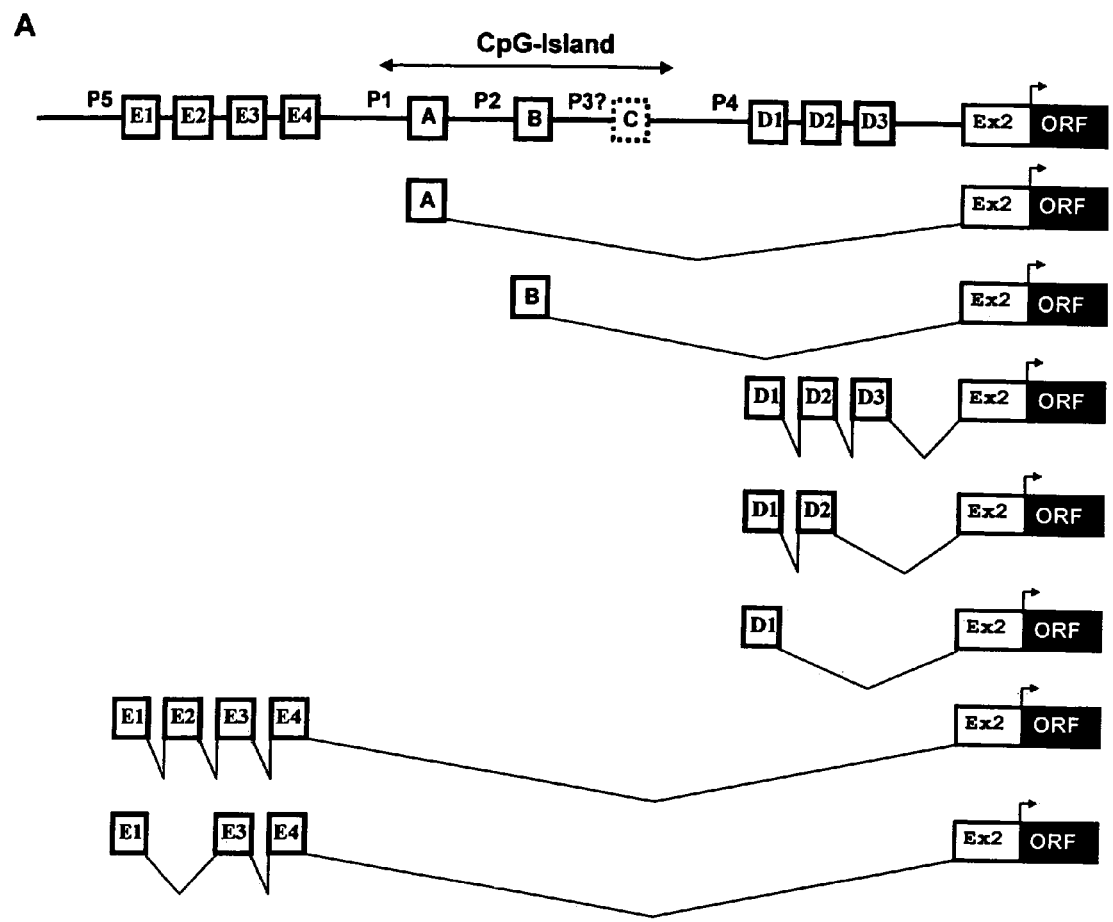
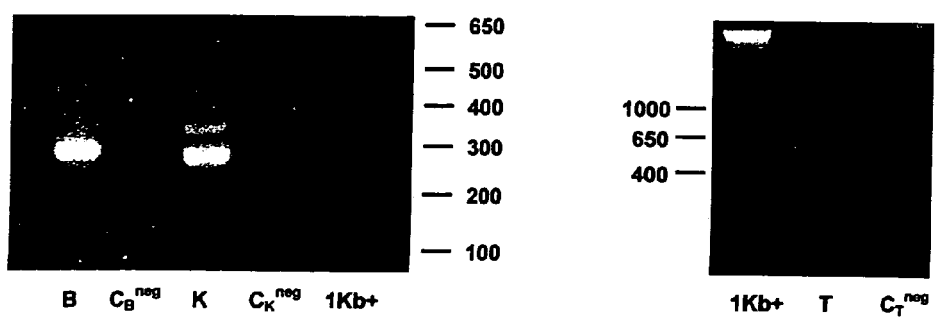

Figure 2
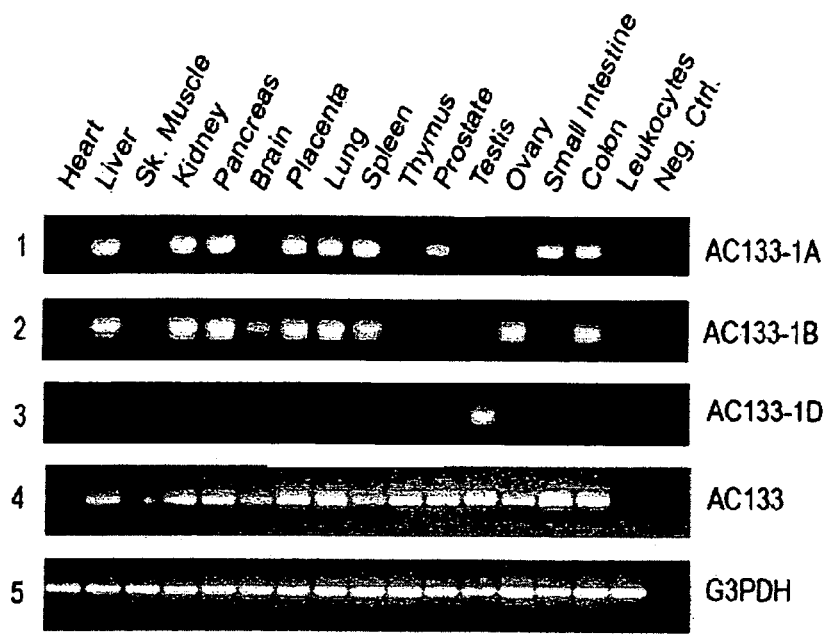
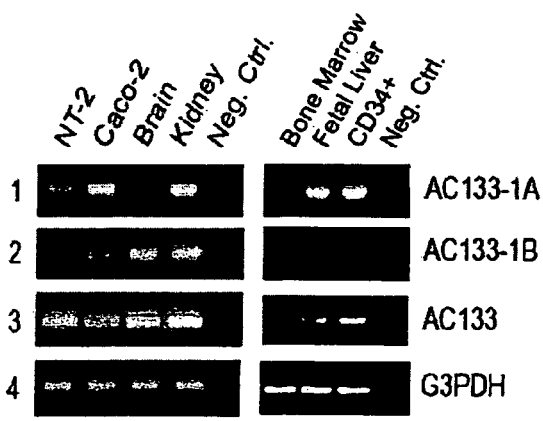
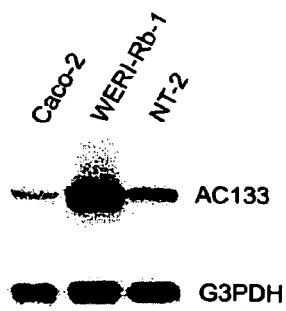

Figure 3A

```
   0  TGCACTCTCCCTTTCCCAAGCCACAAGGCTGCTGCTGCTGGGGGATGGAGGACTGGCGGCATTGGCAAATCAAAACTGTCTTTCCTGGCTCTTCAGTGC
                                                              C/EBPα                            -1800P1
 100  CTCTTTCAGTAATATGAAATTAAAACCAGGTATTGTGGTTACTCACCTGATTTTTGGTTCTTATAAAGGTGCTTTTTGTGTGTGTAGATAGCAGTTAAAT
 200  TGTGTTCCTAGCCGGGGTGGGGGGTGGGTGGTCAAACCTTCTATTTGACCATCTTGCTTCACCCCTTTCTACTGATACTATTGTTGTTGATATTATTAGG
           Sp1
 300  AATGAAAATGAGCCCTGTGAGTTATAAATTGTCTTCATTTTGCAGACCAGGAAACTGAGGCTCAGAGAAATATTAAGCAGCCAAAGTCACAGCGATTAAAA
                                                  ICSBP            NF-1
 400  GAGGCGGGACCAAACTTTGACGGAGATCAGGACCCACTCCTTTGAGAAATCACCTCTTTTGCTAGCTCCAGCCTAAAAGTGCTATCTAGGAGAAGGTTTA
           Sp1                                   C/EBPα
 500  TGGGACCCCAGCAGATGTTCAACCAGAAACTTCTGACCTGCAGGGGCTGCAGAGGGAAATCTGCCCTGATTAGAAGAGATTTGTTTTCCACCCATATTA
                                    HSE-bind
 600  GTTTGATCTCACATTGCTATAAAGAACTACCTGAGACTGGGTTTCAGAGGCTGTACCGTAGGCATGGCCAGAGAGGCTTCAGGAAACTTACAATTATGGT
 700  GGAAGAAGGGAAAGCAAGCACATCTTCACATGGCAGAAGGAGAGACAGAGCGAGCAAAGGGGAAGTGCCACACACTTTAAATCATCAGAAATCCTGAGA
                                                                                           -1100P1
 800  ACTCACTCACTATCATGAGAACAGCAAGGGAGAAATCCGCCCTCATAATCCAATCACCTCCCACTAGGTCCCTCTCCCAGTGAATTATAATTCAATATGA
 900  GATTTGGATGGGACACAGAGCCAAACCATCTAACCTTGCCATGTCCTACTGTACTTTTTGGAAGTTTTCTGAACTAACATTTCTTGTCTAGAAATATAC
1000  ACACTCAAGATCAATCTAACTATTAAAACAAAAAATGCTTATTTTCCAGTACCTGTTTATGTTAGATTCTGGGGTAAAAGAAAAAGGTACTGACTTA
                                     Hb                                                        MRF4
1100  ATGTTCCTGTCTATCATTCATTTGTAGCTTGTGCATCCATCCTTTCATCTGTCTATCCATATCACAAACATGTATTAAACACCTGCTGTATGCTAGACAC
                                      -750P1                                                      E1
1200  CATCCTGAAGGTGCATTTCTTCCCTAAGTCTTTTTTTTGCCTGCCGGAGAGTACAGTATTCTCAATTCAAGATAAGAAGTGGTGAATAAGAGTGAAGTGC
                                        C/EBPα
1300  AAATTGGTGAGGACACTTAGACACCGAGTGATTACTTCTGACAGGTTTCCACCACTCAGCTAAGTAGCAAGGTGAAGACTCCGAGGTTGAGTTGTAACTC
1400  ACAGAGCGGGAAGACCAATAGGCAGTGAGAAAAGAAGTTGCAGTGGCTTCACGTTATAGCAGATGCCTGTGTGTACACATGGGAGCGAATATGGCTTTAT
      -490P1
1500  GCTGTTTTTCAACCGCTTCAGCCACTAGCATTGGTACTGCTGCACACTAAGGATCCAAATGATTGTTTTTTGTTTTTTGTTTTGTTTTGTTTTGTTTTG
                                                  -349P1              Hb
1600  TTTTGTTTAAATTGCATTGGGATTAGGCAACAGAAGGGTCTAATGCGGCCGGGATGAGACAGGAGAGTTTTTAGGAGGGTAGCTGCATTCTAAGTAAGG
1700  GACTCTGCGGGGGAAAAGAGGCGCAAGCGTTGCAAGAAGGGAGTGCAGGGGGTTGAGCAGGCACCTCTACAGGAAATGGATGCTGTCCAGGTGCTGGTG
                                                                                             Exon1A
1800  GGCGCCCCAGGGCTACGTGGCGAAGCAGCTCAGCCGGTCCAATCAGAGTGCGTCCAGGGCTCGGGTTTCGCGATCTTTAAGTGACTGAGGCAGATCCCCA
                                          P2-5'
      β
1900  CGCGGCACCTGGCCATGCTCTCAGCTCTCCCGCCGCCGTGAGTATGTTTAAGGAATCCTTTCCATTACGGCGGCCCCATACCTAGGTCCCGTCGGGAC
      P1-3'
2000  AGAGGAAGCCGCAACGGGTCCCCCGGGCACCCGGGCCTTTCTCCTGCCTCCCGCCACGTCCGAGGGTCCGGCCGCAGCGCCGCCTGAGCCCCTCCGCGG
                                                         Sp1             Sp1
                                                                                             Exon1B
2100  CCGGCAGTGGGAGGCGGGCTCTCCGAAAGCCGTCGCGGTGGTCCCAGAAGCCGGGTCATAAATAATTCACGAGCCAGGGTCTGGCGAGCTAAGGGAAGGG
           Sp1        Sp1                                                                      P2-3'
2200  CGGCGGCAGCGGTGACTAGGGCGGGAGCAGGAGCGGGAGCCGGGTGCACGGTGAGTAGCTGGGTCCTCATCCCGGAGCGAGAGAGGCATCTGCTGACCAG
      P3-5'
                    Sp1
2300  GCGCGGGGCTGAGCGCACTCCTTCCACTGTACTGGGGGTGTACAGTGAGGAGTGGACGGGTTCGCTCTGCGCCCCCTTACCCTAGCCATCTGCGCCGCC
           Sp1   MyoD                              Exon1C                                 Sp1
2400  TCCCTGGCCCCTCAGGAGGTGGTGCGGGCCCGGACAGCGGCTGGGGCCAGGGAACTGCGGCGAGAGCCTGGTGGTGCCGGTGCCGTCCAACCCAAAC
                 E1      Sp1                                     Krox-20
2500  TTTTTAGTCTGAGTGGTGGCCCCGCGACGCCCCGCTTGGGTCTTCTTTCCATCCACTGGGGATGGGGCGGGGTGGGGGTAGCCGGCGGCCGTGGTTCCG
                                                                                        Sp1  CACCC-b1
2600  GAGCGGGAGTCGGAGGTGAGTGTGCGAACTGGACCGGGGCCCCAGAGACTTCGGACTCGCTCTCGGGGAGAATCGGTGACCGAGGTGAGACTCGCCAGGGT
                          P3-3'
```

Figure 3B

```
       GATA-1
0   GACAGACCCCAGATAGCCTTCCAGCTGCGTGCCAGGTGCTTTACCTATTAGATCGCTAGCCTGCGAACCCTATGCGAAATCCTCCTTTGACAGAGGAGCA
       GATA-2

100 GAAGAAGGGTTGGAGAATTCAAACAACTGTCATCTTGGCAGAGTTAGTAAGGGGGACCAGAGCCCCCTTACTGTTGCTGTTGTCTGTCTATTCAGCAGTG
                       SRY

200 CCCTTTAGTTTATTCTTGTTTTTTTTTTCATGTGTTCCATAATTTTTTTCTAAACTTCCTTCTGATTTCTAAACTTTTCTAAACTTCTTTCTGATTTCTA
                                    CdxA                       CdxA

300 AACTTCCTTCTGATTTTTATACGAGACAGTTTCTTTGGGTTTAGTACAATGAGGTGAACAAATGCATCAGAGGACAAGCTGAAAACTTTAAACCAAGTT
             CdxA            SRY

400 GGTACTGTTTAAAATGAAAAGGAAATAGGTTTTTCAGGGAGCAAAGAGCTATTTCTGAGATTTGTTAAGGGTCAAGATACTTTGTTAAAACAGTGGAAGC

500 TGAGTCGGGGGTAATTTTTAGAAATAAAAGGACTTCTTGGATTCTGTAAGTTGCCTGTTCACTCTGATGGTAGTTTCTTTTGCTCTGCAGAAGCTCSRYA

600 GTTTAATTAGATCCCATTTGTCAATTTTGGCTTTTGTTGCCATTGCTTTTGGTGTTTTAGACATGAAGTCCTTGCCCATGCCTATGTCCTGAATGGTATT

700 GCCTAGGTTTTCTTCTAGGGTTTTTATGGTTTTAGGTCTAACATTTAAGTTTTTAATCCATCTTGAATTAATTTTTGTATAAGGTGTAAGGAAGGGATCC
                                             CdxA

800 AGTTTCAGCTTTCTACATATGGCTAGCCAGGTTCCAGCACCGTTTGTTGGGAATTGAACAATGAAAACACTTGGACACAGGAAGGGGAACATCACACA
                                  GATA-2                   Sox-5
           MZF1

1000 CCGGGGCCTGTTGTCAGGTGGCGGGAGTGGGGAGGGATAGCATTAGGACATATACCTAATGTAAATGACGAGTTAATAGGTGCAGCACACCGACATGGCA
                                                              CdxA

1100 CATGTATACACATGTAACAAACATGCACATTGTGCACATGTACCCTAGAACTTAAAGTATAATAAAAAAATATATATACATATACATATATATATGTATA
     CdxA

1200 TGTATATATATAAAAGGACTTCTTGAAAGGATGGTCCCTGGGTGGCTTAGGTAAGTGGCAGCAAGGCTGGCTAGCCAGGCTTAGGAATCTAGGACATGCC
     GATA-1

1300 ACAGGACCCCTGATGGGTGGGTGGCTGCGGCTGCCAGAACAGGACCCTGGATGTGGCTACTGGCATTGCTGCCATCATTGCTGGAATGAATTAGATACTG
                                                GATA-2             Exon1D1
1400 TCCTGCTTCAGAGTGCGCAGGCCCAGGCCCAGAAGAAAGCTTCTGATTGGCCCAGCATGGCTCAGCTCCACCAGGACACAGTTTGGGCGCCTCAGCTGAC
                                                        NF-kappaB                     HNF-3b
1500 CTCACAATGCAAGGCAGGGCTGCCTCCCACCCAGCTCACAAACGTGGTCTCAGATGTTGGGTATCCCCATGCCCTCGCCAAAAGCAGTGGCAGTCAGAA
                                                                                         YY-1

AAATCCACTACAAAGCTCTTCTTTAAAAAGAAAGATTCTGAGAAGTTCCATCAAAAGAAGAAAAGAAGAAATGAAGGTGATTGATCACCATATTTGCTTT
```

Figure 3C

```
   0  GCATGTCTGTCTCTGTGTCCAAATTTTCCCTTTTTAAAAAGGCACTAGCCATAATGGATTAGGGTTCACCATAATGAGTTCATTTTAACTAAACAAATTA
                                                                 MZF1              Oct-1           SRY

100  CCTCTATAAACACCCTGTCTCCAAATAAGGTCACATTCTCTGGTACTGGGGATTGGGACTTCAATGTATGAGTGTTTTGGGGCACACCAGTTAGCCCGTA
                                                       GATA-1

200  ACAGGGTAGCTGCAATGATGACAGGAAATCAGGGATGGGTAAGCATTCATAAATGTCACTCTCCTAGAGGAAAGGGAGGCTTCCTTTCGGGGACATTTTT
                                                          CdxA

300  TGTCCTCATCTTGCCTGGGTTATAGAAGCAACTCACATAGGATTTTTGCTGGGTGAGTCAGCTACCCTACTGCAGAATGTTCCACTGTACAGTGTGGGAG
                                                            AP-1              HSF2              Lyf-1

400  GAGGTTGGCTGTAAACTCAGCATAAAATGTCATAGTGGTCCCAACTCAGCAATAAATGTCATAGGGCACCCCGGCTGGGTGAATTCTTCCAGACCCTGTT
          MyoD                                         CdxA

500  TTCTCTTCCTCATGCTTCAGACCTCTTCATTTCACAAGCAGTCTGTTGAAGTGAGATAACTCCCAGGCCCAGAGTCAGCCAATCTGCATTTCAACCCCCC
                                                            GATA

600  ACCTCCATTCCTCAGCAATGGCCCTTCATCTTGGAAATCAGATAATAATCACAGCCTCTATGCCTGAATTAAAGTTTGCTCTTGTATCTTCTTTACCAAGT
                                              CdxA

700  TTACATATACTCAATATTGGTGTATACAACTATGTAATGCAGTATGACCTCTCTCTGTCTCTGTTCTCCTGGCAACTCATTCAGGCTCCATTCCCTTCAT

Nkx-2                                                                      GATA-1
 800  ATCCCACTTGAATTTGCACTACTCTGCACCACTGACTTTAGAATCTGTCTTGTAAATAGGGTCAGAGTTCCTCAGCCAGATCCCGATGGGTAAAAGGAAC
          MZF-1                                                    Lyf-1
 900  CATGTCCCCACCCTGAGTTGAGCAGGTCTTCAAGAAACCCTCTTGTGAGTCCACTCTGCCCCAAAGCTGCCTCCCAAAGATGCAGCATCTGTCCTGGCAG
                                                                      GATA-2    deltaE
1000  AGTGTGGGCAGGAAGGCTGCCTTGCCAGGCTCCTGACTCCCAGTGCTGCGTGGTGCTGATGAGCTGAGCTGATCTTTGAGGGCCAGACCAGGTGAAAGT
                                                                            MZF-1
1100  TCCCACCCTAAGCAGCTCAGGGCAGGGACAGACCAAATCCAAGTGCACCAAATGGGGCCATGAGAAACCCTCCTGTGGGGATATCTGTGATCTCAGGAAT
                                            c-Rel                     Exon1E1
1200  GACCCTGAGAGGACACTGCTCTGATGCTCTGATGAGACTGAGGGGGATTCCAAGCTTCCAGGGTGCTGGGCAGTGTCTCCCCAGAGAGTGGCTGTTCCCA
                                            c-Ets-1
1300  GTGTCAATCAGGCAGGAAGGGTAGAATGCTGGGACAGGAAGTAGCTTGGAGGTGGGCCTTAGGCTGGTAGAAGTTGCTGCTTTCTTCTCTGTGGGCTCCT
                                                                        GATA-1
1400  TTCTCGTGGATCTGGACCCCAGGAGTTCCCAGGCATAGAGAGGAGGGGTGCCAGGTGATGGGGGTGATGGAGGCGGTGGCCACGGCCCTGGAGAAGGCTG
```

STEM CELL-SPECIFIC PROMOTERS AND THEIR USE

This application claims benefit of U.S. Provisional Patent Application Ser. No. 60/516,229, filed Oct. 31, 2003.

The subject matter of this application was made with support from the United States Government under National Heart Lung & Blood Institute Grant No. RO1 HL61849. The United States Government has certain rights.

FIELD OF THE INVENTION

The present invention is directed to stem cell-specific promoters and their use.

BACKGROUND OF THE INVENTION

Rapid revascularization of injured, ischemic and regenerating organs is essential to restore organ function. The angiogenic switch initiates the revascularization process and involves recruitment of endothelial cells that assemble into neovessels (Folkman et al., "Angiogenesis in Cancer, Vascular, Rheumatoid and Other Disease," Nat. Med. 1:27-31 (1995); Folkman et al., "Therapeutic Angiogenesis in Ischemic Limbs," Circulation 97:1108-1110 (1998); Hanahan et al., "Patterns and Emerging Mechanisms of the Angiogenic Switch During Tumorigenesis," Cell 86:353-364 (1996); Risau, W. "Mechanisms of Angiogenesis," Nature 386:671-674 (1997); Yancopoulos et al., "Vascular-specific Growth Factors and Blood Vessel Formation," Nature 407: 242-248 (2000); Carmeliet et al., "Angiogenesis in Cancer and Other Diseases," Nature 407:249-257 (2000); Pepper et al., "Manipulating Angiogenesis. From Basic Science to the Bedside," Arterioscler. Thromb. Vasc. Biol. 17:605-619 (1997). Much effort has been focused on delivering aniogenic factors to accelerate tissue revascularization (Isner et al., "Myocardial Gene Therapy," Nature 415:234-239 (2002); Khurana et al., "Insights from Angiogenesis Trials Using Fibroblast Growth Factor for Advanced Arteriosclerotic Disease," Trends Cardiovasc. Med. 13:116-122 (2003); Cao et al., "Angiogenic Synergism, Vascular Stability and Improvement of Hind-Limb Ischemia by a Combination of PDGF-BB and FGF-2," Nat. Med. 9:604-613 (2003); and Carmeliet, P., "VEGF Gene Therapy: Stimulating Angiogenesis or Angioma-Genesis?" Nat. Med. 6:1102-1103 (2000). However, because tissue injury is associated with disruption of a permissive microenvironment necessary for recruiting preexisting endothelial cells (ECs), exogenous introduction of vascular progenitors may facilitate restoration of organ revascularization. Accumulating evidence suggests that bone marrow contains vascular progenitor cells that can mobilize to ischemic sites and complement neo-angiogenesis afforded by pre-existing endothelium, thereby restoring rapid and timely organ revascularization.

Adult bone marrow is a rich reservoir of tissue-specific stem and progenitor cells. Among these, a scarce population of cells known as EPCs can be mobilized to the circulation and contribute to the neoangiogenic processes. Circulating EPCs (CEPs) have been detected in the circulation either after vascular injury or during tumor growth. CEPS primarily originate from EPCs within the bone marrow and differ from sloughed mature, circulating endothelial cells (CECs) that randomly enter the circulation as a result of blunt vascular injury. It is possible, however, that the parenchyma of the systemic vasculature or certain organs may harbor endogenous EPC-like cells. For example, distinct side population stem cells within the skeletal muscle can differentiate into ECs (Majka et al., "Distinct Progenitor Populations in Skeletal Muscle are Bone Marrow Derived and Exhibit Different Cell Fates During Vascular Regeneration," J. Clin. Invest. 111:71-79 (2003). Therefore, CEPs may originate either from bone marrow-derived EPCs or from resident EPCs embedded within organs and the systemic vasculature. Endothelial progenitor cells residing in the bone marrow will be referred to as EPCs, while endothelial progenitors detected in the circulation will be referred to as CEPs.

Emerging evidence suggests that angiogenic factors recruit subsets of proangiogenic hematopoietic cells, including hematopoietic stem cells (HSCs) and hematopoietic progenitor cells (HPCs). Corecruitment of HSCs and HPCs, along with EPCs and CEPs, may contribute to the initiation and sustenance of neoangiogenesis. The physiological role of corecruited HSCs and HPCs in formation of long-lasting functional neovessels remains to be determined.

Several studies have shown that bone marrow-derived cells functionally contribute to neoangiogenesis during wound healing and limb ischemia (Majka et al., "Distinct Progenitor Populations in Skeletal Muscle are Bone Marrow Derived and Exhibit Different Cell Fates During Vascular Regeneration," J. Clin. Invest. 111:71-79 (2003); Asahara et al., "Isolation of Putative Progenitor Endothelial Cells for Angiogenesis," Science 275:964-967 (1997); Asahara et al., "Bone Marrow Origin of Endothelial Progenitor Cells Responsible for Postnatal Vasculogenesis in Physiological and Pathological Neovascularization," Circ. Res. 85:221-228 (1999); (Asahara et al., VEGF Contributes to Postnatal Neovascularization by Mobilizng Bone Marrow-Derived Endothelial Progenitor Cells," EMBO J. 18:3964-3972 (1999); Iwaguro et al., "Endothelial Progenitor Cell Vascular Endothelial Growth Factor Gene Transfer for Vascular Regeneration," Circulation 105:732-738 (2002); Kalka et al., "Transplantation of ex vivo Expanded Endothelial Progenitor Cells for Therapeutic Neovascularization," Proc. Natl. Acad. Sci. USA 97:3422-3427 (2000); Schatteman et al., "Blood-Derived Angioblasts Accelerate Blood-Flow Restoration in Diabetic Mice," J. Clin. Invest. 106:571-578 (2000); Crosby et al., "Endothelial Cells of Hematopoietic Origin Make a Significant Contribution to Adult Blood Vessel Formation," Circ. Res. 87:728-730 (2000); Takahashi et al., "Ischemia- and Cytokine-Induced Mobilization of Bone Marrow-Derived Endothelial Progenitor Cells for Neovascularization," Nat. Med. 5:434-438 (1999); Luttun et al., "Vascular Progenitors: From Biology to Treatment," Trends Cardiovasc. Med., 12:88-96 (2002); Rafii et al., "Circulating Endothelial Precursors: Mystery, Reality, and Promise," J. Clin. Invest. 105: 17-19 (2000), postmyocardial infarction (Orlic et al., "Bone Marrow Cells Regenerate Infarcted Myocardium," Nature 410:701-705 (2001); Orlic et al., "Mobilized Bone Marrow Cells Repair the Infarcted Heart, Improving Function and Survival," Proc. Natl. Acad. Sci. USA 98:10344-10349 (2001); Kocher et al., "Neovascularization of Ischemic Myocardium by Human Bone-Marrow-Derived Angioblasts Prevents Cardiomyocyte Apoptosis, Reduces Remodeling and Improves Cardiac Function," Nat. Med. 7:430-436 (2001); Jackson et al., "Regeneration of Ischemic Cardiac Muscle and Vascular Endothelium by Adult Stem Cells," J. Clin. Invest. 107:1395-1402 (2001); Edelberg et al., "Young Adult Bone Marrow-Derived Endothelial Precursor Cells Restore Aging-Impaired Cardiac Angiogenic Function," Circ. Res. 90:E89-E93 (2002), endothelialization of vascular grafts (Shi et al., "Evidence for Circulating Bone Marrow-Derived Endothelial Cells," Blood 92:362-367 (1998); Bhattacharya et al., "Enhanced Endothelialization and Microvessel Formation in Polyester Grafts Seeded with CD34+Bone Marrow Cells," Blood 95:581-585 (2000); Kaushal et al., "Functional Small-Diameter Neovessels Created Using Endothelial Progenitor Cells Expanded ex vivo," Nat. Med. 7:1035-1040 (2001); Noishiki et al., "Autocrine Angiogenic Vascular Prosthesis with Bone Marrow Transplantation," Nat. Med. 2:90-93 (1996), atherosclerosis (Sata et al., "Hematopoietic Stem Cells Differentiate into Vascular Cells that Participate in the Pathogenesis of Atherosclerosis," Nat. Med. 8:403-409 (2002), retinal and lymphoid organ neovascularization (Otani et al., "Bone Marrow Derived Stem Cells Target Retinal Astrocytes and Can Promote or Inhibit Retinal Angiogenesis," Nat. Med. 8:1004-1010 (2002); Grant et al., "Adult Hematopoietic Stem Cells Provide Functional Hemangioblast Activity During Retinal Neovascularization," Nat. Med. 8:607-612 (2002); Crisa et al., "Human Cord Blood Progenitors Sustain Thymic T-Cell Development and a Novel Form of Angiogenesis," Blood 94:3928-3940 (1999), vascularization during neonatal growth (Young et al., "VEGF Increases Engraftment of Bone Marrow-Derived Endothelial Progenitor Cells (EPCs) into Vasculature of Newborn Murine Recipients," Proc. Natl. Acad. Sci. USA 99:11951-11956 (2002) and tumor growth (Asahara et al., "Bone Marrow Origin of Endothelial Progenitor Cells Responsible for Postnatal Vasculogenesis in Physiological and Pathological Neovascularization," Circ. Res. 85:221-228 (1999); Lyden et al., "Impaired Recruitment of Bone-Marrow-Derived Endothelial and Hematopoietic Precursor Cells Blocks Tumor Angiogenesis and Growth," Nat. Med. 7:1194-1201 (2001); Reyes et al., "Origin of Endothelial Progenitors in Human Postnatal Bone Marrow," J. Clin. Invest. 109:337-346 (2002); Moore, M. A., "Putting the Neo into Neoangiogenesis," J. Clin. Invest. 109:313-315 (2002); Gehling et al., "In vitro Differentiation of Endothelial Cells from AC133-Positive Progenitor Cells," Blood 95:3106-3112 (2002); Marchetti et al., "Endothelial Cells Genetically Selected from Differentiating Mouse Embryonic Stem Cells Incorporate at Sites of Neovascularization in vivo," J. Cell. Sci. 115:2075-2085 (2002); Davidoff et al., "Bone Marrow-Derived Cells Contribute to Tumor Neovascular and, When Modified to Express an Angiogenesis Inhibitor, Can Restrict Tumor Growth in Mice," Clin. Cancer Res. 7:2870-2879 (2001)).

These studies have introduced the concept that vascular trauma and organ regeneration results in the release of chemokines that recruit EPCs and CEPs to the neoangiogenic site. Rapid incorporation of EPCs and CEPs accelerates vascular healing and prevents potential vascular complications secondary to thrombosis and hypoxia. Tissue ischemia results in upregulation of angiogenic factors, including vascular endothelial growth factor (VEGF)-A, which through interaction with its receptors VEGFR2 (KDR or Flk-1) and VEGFR1 (Flt-1) expressed on EPCs, CEPS, HSCs and HPCs, promotes migration of these cells to the site of the injury.

Despite the contribution of bone marrow-derived progenitors to tissue revascularization in animals models, the importance of these cells in restoring organ vascularization in a clinical setting remains unknown. Several recent clinical trials have challenged the potential of bone marrow-derived cells in restoring vascularization of ischemic tissues. The success of these strategies depends on defining the mechanisms by which stem and progenitor cells undergo appropriate molecular and differentiation, thereby permitting their functional incorporation into adult tissues.

The present invention is directed to overcoming the deficiencies in the art by providing a promoter which functions only in stem cells and not in other cell types to facilitate recovery and study of stem cells and to achieve therapeutic benefits.

SUMMARY OF THE INVENTION

The present invention relates to a method of isolating stem cells from a mixed population of different cell types. This method involves selecting a promoter which functions only in said stem cells and not in the other cell types. The promoter can have a nucleotide sequence selected from the group consisting of SEQ ID NO: 4, SEQ ID NO: 5, SEQ ID NO: 6, SEQ ID NO: 7, and SEQ ID NO: 8. A nucleic acid molecule encoding a marker protein under control of said promoter is introduced into all cell types of said mixed population and only the stem cells, but not the other cell types, within said mixed population are allowed to express said marker protein. The cells of said mixed population of cell types that are expressing the marker protein, which are restricted to the stem cells are identified and separated from the mixed population, where the separated cells are restricted to the stem cells.

The present invention also relates to a population of cell types enriched in stem cells. All cell types in the population contain a promoter which functions only in the stem cells and has a nucleotide sequence selected from the group consisting of SEQ ID NO: 4, SEQ ID NO: 5, SEQ ID NO: 6, SEQ ID NO: 7, and SEQ ID NO: 8.

A further embodiment of the present invention is directed to a promoter having a nucleotide sequence selected from the group consisting of SEQ ID NO: 4, SEQ ID NO: 5, SEQ ID NO: 6, SEQ ID NO: 7, and SEQ ID NO: 8.

Another aspect of the present invention is directed to an isolated nucleic acid construct which includes a promoter which functions only in stem cells, a nucleic acid encoding a protein, and a 3' control region. The promoter, the nucleic acid encoding a protein, and the 3' control region are positioned with respect to one another to permit expression of the protein, where the promoter has a nucleotide sequence selected from the group consisting of SEQ ID NO: 4, SEQ ID NO: 5, SEQ ID NO: 6, SEQ ID NO: 7, and SEQ ID NO: 8. Expression vectors, host cells, and transgenic animals containing this nucleic acid construct are also disclosed.

The present invention is also directed to a method of monitoring stem cell movement in a transgenic animal. This method involves providing a transgenic animal containing the above described nucleic acid construct and identifying locations in the transgenic animal which express the marker protein at different periods of time. The locations identified correspond to where stem cells are located at the different periods of time.

Yet another embodiment of the present invention relates to a method of treating a patient having a disorder mediated by cell proliferation. This is carried out by administering to the patient a nucleic acid construct comprising a promoter which functions only in stem cells and a nucleic acid encoding an enzyme capable of converting a prodrug to a cytotoxic drug. The promoter has a nucleotide sequence selected from the group consisting of SEQ ID NO: 4, SEQ ID NO: 5, SEQ ID NO: 6, SEQ ID NO: 7, and SEQ ID NO: 8. The prodrug is also administered to the patient. This method is carried out under conditions effective for the enzyme to be expressed and to convert the prodrug to the cytotoxic drug so that the disorder mediated by cell proliferation is treated.

BRIEF DESCRIPTION OF THE DRAWINGS

FIGS. 1A-C show the genomic structure of the promoter region of human AC133 and alternative splicing within its 5'-UTR. FIG. 1A shows that exon 1A, exon 1B, exons D1, D2, and D3 from cluster 1D, and exon E4 from cluster 1E are alternatively spliced to a common exon 2, according to RACE data. The translation initiation site is located in exon 2. 5'-RACE revealed the presence of exons 1A, 1B, and exon clusters 1D and 1E, while exon 1C was found as a single EST from skeletal muscle. P1, P2, P4, P5, and, possibly, P3 are alternative promoters for the AC133 gene. Exons 1A, 1B, 1C and their corresponding promoters are located within a CpG island. FIG. 1B is a 5'-RACE analysis of AC133 mRNA. mRNAs from brain [B] and kidney [K] were subjected to 5'-RACE analysis. The PCR products (second round of amplification; nested primers) were resolved on 1.5% agarose gel, stained with ethidium bromide. Size marker 1 Kb Plus is shown on the right [1 Kb+]. $C_B^{neg}$ and $C_K^{neg}$ are negative controls for brain and kidney correspondingly. One band from brain and two bands from kidney were isolated, subcloned into pCR4-TOPO and sequenced. The band from brain was found to comprise exon 1B fragments. The lower band from kidney was found to comprise a majority of exon 1A fragments, with a minority of exon 1B fragments. The upper band from kidney was found to comprise exon 1A fragments from an alternate transcription start point, 55 bp longer than those in the lower band. FIG. 1C is a 5'-RACE analysis of AC133 mRNA in testis (T). Multiple bands were observed for testis 5'-RACE products. Since multiple bands were observed, the entire pool of PCR products were subcloned into pCR4-TOPO directly from the PCR product mix. PCR mix was determined to contain five different alternative splice variants containing exons from either cluster 1E or cluster 1D.

FIGS. 2A-C show the tissue distribution of different 5'-UTR isoforms of AC133 mRNA. AC133 isoforms were amplified by PCR and separated on a 2% agarose gel stained with ethidium bromide. Panels A4 and B3 show expression of AC133 by RT-PCR with primers located in the 3'- distal exons common to all known AC133 isoforms in indicated tissues or cell lines. FIG. 2A shows that the expression of exon 1A, exon 1B, and exon 1D containing isoforms of AC133 mRNA in human adult tissues is represented in panels A1 and A2. FIG. 2B shows that the expression of exon 1A, exon 1B and exon 1D containing isoforms of AC133 mRNA in human brain, kidney, bone marrow, fetal liver, CD34+cord blood cells and cell lines Caco-2 and NT-2 are represented in panels B1 and B2. Results are consistent in at least three independent PCR reactions. FIG. 2C is a Northern blot analysis of total RNA isolated from Caco-2, WERI-Rb-1, and NT-2 cell lines. Equal amounts of RNA (20 µg) were loaded in each lane. The blot was hybridized with a $^{32}$P-labeled probe for human AC133 mRNA. Size positions of RNA Ladder are indicated on the right side. A $^{32}$P-labeled probe for human glyceraldehyde 3-phosphate dehydrogenase (G3PDH) was included as an internal control for loading and is shown in the bottom line.

FIGS. 3A-C show the genomic nucleotide sequence of the 5'-UTR and promoter regions of AC133 gene. Frames highlight exons. Putative transcription binding sites are underlined or top lined. Bold underlined nucleotide letters indicate either 5'- or 3'-end sites for different AC133 promoter constructs. Mapping based on AliBaba2.1 and TFsearch provides a prediction for 90-100% matches only. The accession number in GeneBank is AY275524. FIG. 3A is a genomic nucleotide sequence of promoters P1, P2, and P3 (SEQ ID NO: 1). FIG. 3B is a genomic nucleotide sequence of promoter P4 (SEQ ID NO: 2). FIG. 3C is a genomic nucleotide sequence of promoter P5 (SEQ ID NO: 3).

FIG. 4C is a functional analysis of human AC133 promoter 1 [P 1] activity using 5'-/3'-deletion constructs in Caco-2 and NT-2 cell lines. The diagram on the left side shows different reporter constructs made from the 5'-flanking region of exon 1A, using primers listed in Table 1. Transcription start point is indicated by +1. Luciferase gene is fused to: +10 position of P1 in constructs A, B, D, F and H; –250 position of P1 in constructs E and G. In construct C, the most active fragment of P1 is placed in reverse orientation, with luciferase fused to position –1100. The diagram on the right side shows fold increase in activity of the promoter constructs compared to promoter-less pGL3-Enhancer vector [construct I]. All data represent the mean of three independent experiments.

DETAILED DESCRIPTION OF THE INVENTION

Figure 4:
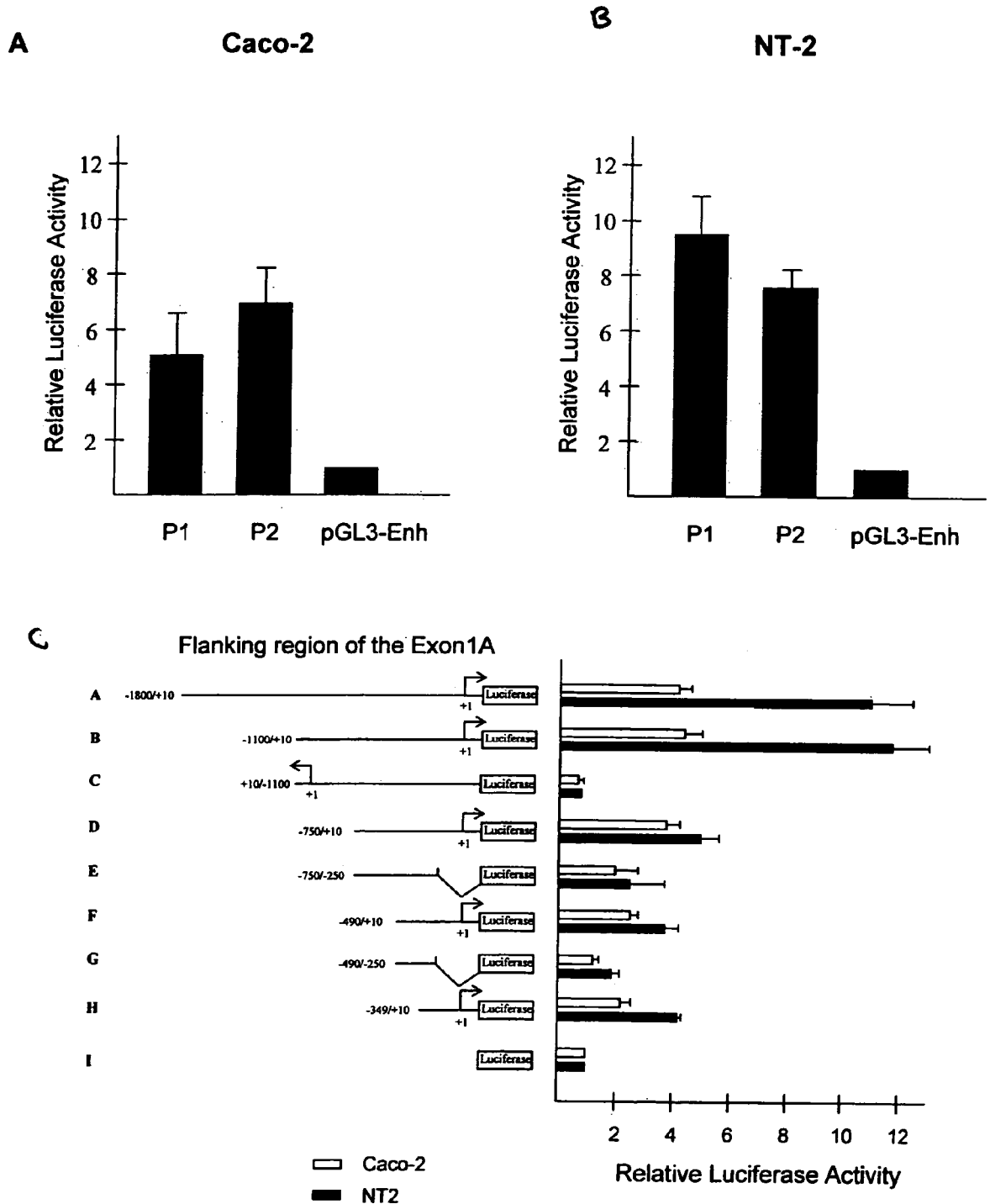
FIGS. 4A-C show the functional analysis of human AC133 promoters. Functional analysis of promoters P1 and P2 in Caco-2 and NT-2 cell lines are shown in FIGS. 4A and B, respectively. Bars show fold increase in activity of luciferase for the constructs cloned into pGL3-Enhancer vector containing promoters P1 or P2, compared to promoter-less pGL3-Enhancer vector. All data represent the mean of at least three independent experiments.

The present invention is directed to a promoter which functions only in stem cells. The promoter has a nucleotide sequence selected from the group consisting of SEQ ID NO: 4, SEQ ID NO: 5, SEQ ID NO: 6, SEQ ID NO: 7, and SEQ ID NO: 8 as follows.

The promoter of SEQ ID NO: 4 has the following nucleotide sequence:

```
GGTACCTAAGGGGAAGGAAAACATCCTCTTTACTTTTCCTTCTGCTTTTG
TCAAGCAGAAGGAGTCTCTCACATTAGCCACCACAGTTGGGAATATACTG
GGTCTCACCTGAAACCAGCAGATCTCAGAGTCACACCCAAGAACCACAGT
GTACTACCTGAGTATTGCTTCTGGCTATTGAGAACCCAAGGGCTCTTTAG
CCAACAGGTGATGGGTCCTGCCCAGACTGTTTCTTTCCCTTCAAGGCAGC
AGTTTCCCTTCTGGCCCAGGATGTGTCTAGAAATGTTATCCACAAGTTAG
GACCTGGGATGGGGTCTGATGACTCAGACTGATGCCCTGTCCTACTGTG
GCTAAACTGATATTCAAGATAACAAAGTCCTCTTTACTCTTCCCCCTCTT
CTCTTCAAGCAGAAGGAATGGGTCTCTTCGTGCTGTTTTTAATCACTCCA
GCCACTAGCATTGGGACTGATGCAGACACTAAGGATCCAAATGATTATTT
TTGTTTTGTTTTTTTAACTGCATTGGGATTAGGCAACAGAAGGGTCTAAT
GTGGCTGAGAGTTTTTGAGAGAGGAGCATTTTTAGGAGGGTAGCTGCATT
CCAAGTAGAGAGCTCTGCTGGGGTAAAAGAGGCATGAGTGCTAGAAAAGG
GCATGCAGTGATGAAGAGCCACTAACAGCACTACCTGGGGTTGGGGTAGG
GGTGTCACAAGCACTCCCTTAGCTCCCCTGTCTGGTGTCTCAGTAAGTCG
CATGCCCTCCAAGTCTACTGGCTCTGAGCTCAGCATTTGGGCTTGCTTAG
GAGTTGCTGTCCTTGTGGCCTAGGCTGCCTTTAAGGTTATTTGGGGCCCC
AGAGCACTTTACTGAAACTCAAGTTTTCACCACTGGTATGGGCTATTTCC
```

-continued

```
TCTGAGGGAAATTGGCTGAGTTCAGCCTAGTTTTGCTTTCTGCTATGACA
GAGCAGTACTGAGTTCAATTCAAAGTCTCCCAATCACTGCACTCTCCCTT
TCCCAAGCCACAAGGCTGCTGCTGCTGGGGGATGGAGGACTGGCGGCATT
GGCAAATCAAAACTGTCTTTCCTGGCTTCTTCAGTGCCTCTTTCAGTAAT
ATGAAATTAAAACCAGGTATTGTGGTTACTCACCTGATTTTTGGTTCTTA
TAAAGGTGCTTTTTGTGTGTGTAGATAGCAGTTAAATTGTGTTCCTAGCC
GGGGTGGGGGTGGGTGGTCAAACCTTCTATTTGACCATCTTGCTTCACC
CCTTTCTACTGATACTATTGTTGTTGATATTATTAGGAATGAAAATGAGC
CCTGTGAGTTATAATTGTCTTCATTTTGCAGACCAGGAAACTGAGGCTCA
GAGAAATATTAAGCAGCCAAAGTCACAGCGATTAAAAGAGGCGGGACCAA
ACTTTGACGGAGATCAGGACCCACTCCTTTGAGAAATCACCTCTTTTGCT
AGCTCCAGCCTAAAAGTGCTATCTAGGAGAAGGTTTATGGGACCCCAGCA
GATGTTCAACCAGAAACTTCTGACCTGCAGGGGCTGCAGAGGGGAAATCT
GCCCTGATTAGAAGAGATTTGTTTTCCACCCATATTAGTTTGATCTCACA
TTGCTATAAAGAACTACCTGAGACTGGGTTTCAGAGGCTGTACCGTAGGC
ATGGCCAGAGAGGCTTCAGGAAACTTACAATTATGGTGGAAGAAGGGAAA
GCAAGCACATCTTCACATGGCAGAAGGAGAGACAGAGCGAGCAAAGGGGA
AGTGCCACACACTTTTAAATCATCAGATATCCTGAGAACTCACTCACTAT
CATGAGAACAGCAAGGGAGAAATCCGCCCTCATAATCCAATCACCTCCCA
CTAGGTCCCTCTCCCAGTGAATTATAATTCAATATGAGATTTGGATGGGG
ACACAGAGCCAAACCATCTAACCTTGCCATGTCCTACTGTACTTTTTGGA
AGTTTTCTGAACTAACATTTCTTGTCTAGAAATATACACACTCAAGATCA
ATCTAACTATTAAAACAAAAAATGCTTATTTTCCAGTACCTGTTTTATG
TTAGATTCTGGGGTAAAAAGAAAAAGGTACTGACTTAATGTTCCTGTCTA
TCATTCATTTGTAGCTTGTGCATCCATCCTTTCATCTGTCTATCCATATC
ACAAACATGTATTAAACACCTGCTGTATGCTAGACACCATCCTGAAGGTG
CATTTCTTCCCTAAGTCTTTTTTTTGCCTGCCGGAGAGTACAGTATTCTC
AATTCAAGATAAGAAGTGGTGAATAAGAGTGAAGTGCAAATTGGTGAGGA
CACTTAGACACCGAGTGATTACTTCTGACAGGTTTCCACCACTCAGCTAA
GTAGCAAGGTGAAGACTCCGAGGTTGAGTTGTAACTCACAGAGCGGGAAG
ACCAATAGGCAGTGAGAAAGAAGTTGCAGTGGCTTCACGTTATACCAGA
TGCCTGTGTGTACACATGGGAGCGAATATGGCTTTATGCTGTTTTTCAAC
CGCTTCAGCCACTAGCATTGGTACTGCTGCACACTAAGGATCCAAATGAT
TGTTTTTTTGTTTTTGTTTTGTTTGTTTTGTTTTGTTTTGTTTTAAAT
TGCATTGGGATTAGGCAACAGAAGGGTCTAATGCGGCCGGGATGAGACAG
GAGAGTTTTTAGGAGGGTAGCTGCATTCTAAGTAAGGGACTCTGCGGGGG
GAAAAGAGGCGCAAGCGTTGCAAGAAGGGAGTGCAGGGGGTTGAGCAGGC
ACCTCTACAGGAAATGGATGCTGTCCAGGTGCTGGTGGGCGCCCCAGGGC
TACGTGGCGAAGCAGCTCAGCCGGTCCAATCAGAGTGCGTCCAGGGCTCG
GGTTTCGCGATCTTTAAGTGACTGAGGCAGATCCCCAC
```

The nucleotide sequence of SEQ ID NO: 4 is part of GeneBank Accession No. AY275524, which is hereby incorporated by reference in its entirety.

The promoter of SEQ ID NO: 5 has the following nucleotide sequence:

```
CCGGTCCAATCAGAGTGCGTCCAGGGCTCGGGTTTCGCGATCTTTAAGTG
ACTGAGGCAGATCCCCACGCGGCACCTGGCCATGCTCTCAGCTCTCCCGC
CGCGGTGAGTATGTTTAAGGAATCCTTTCCATTACGGCGGCCCCATACCT
AGGTCCCCGTCCGGGACAGAGGAAGCCGCAACGGGTCCCCCCGGGCACCC
GGGCCTTTCTCCTGCCTCCCGCCACGTCCGAGGGTCCGGCCGCAGCGCCG
CCTGAGCCCCTCCGCGGCCGGCAGTGGGAGGCGGGCTCTCCGAAAGCCGT
CGCGGTGGTCCCAGAAGCCGGGTCATAAATAATTCACGAGCCAGGGTCTG
GCGAGCTAAGGGAAG
```

The nucleotide sequence of SEQ ID NO: 5 is part of GeneBank Accession No. AY275524, which is hereby incorporated by reference in its entirety.

The promoter of SEQ ID NO: 6 has the following nucleotide sequence:

```
CGGCGGCAGCGGTGACTAGGGCGGGAGCAGGAGCGGGAGCCGGGTGCACG
GTGAGTAGCTGGGTCCTCATCCCGGAGCGAGAGAGGCATCTGCTGACCAG
GCGCGGGGCTGAGCGCACTCCTTCCACTGTACTGGGGGTGTACAGTGAGG
AGTGGACGGGTTCGCTCTGCGCCCCCCTTACCCTAGCCATCTGCGCCGCC
TCCCTGGCCCCTCAGCAGGTGGTGCGGGCCCGGACAGCGGCTGGGGGCCA
GAGGAACTGCGGGGAGAGCGTGGTGGTGCCGGTGCCCGTCCAACCCAAAC
TTTTTAGTCTGAGTGGTGGCCCGCGACGCCCCGCTTGGGTCTTCTTTCCA
TCCACTGGGGATGGGGCGGGGTGGGGTAGCCGGCGGCCGTGGTTCCG
GAGCGGGAGTCGGAGGTGAGTGTGC
```

The nucleotide sequence of SEQ ID NO: 6 is part of GeneBank Accession No. AY275524, which is hereby incorporated by reference in its entirety.

The promoter of SEQ ID NO: 7 has the following nucleotide sequence:

```
GACAGACCCCAGATAGCCTTCCAGCTGCGTGCCAGGTGCTTTACCTATTA
GATCGCTAGCCTGCGAACCCTATGCGAAATCCTCCTTTGACAGAGGAGCA
GAAGAAGGGTTGGAGAATTCAAACAACTGTCATCTTGGCAGAGTTAGTAA
GGGGGACCAGAGCCCCCTTACTGTTGCTGTTGTCTGTCTATTCAGCAGTG
CCCTTTAGTTTATTCTTGTTTTTTTTTCATGTGTTCCATAATTTTTTC
TAAACTTCCTTCTGATTTCTAAACTTTTCTAAACTTCTTTCTGATTTCTA
AACTTCCTTCTGATTTTTATACGAGACAGTTTCTTTGTGTTTTAGTACAA
TGAGGTGAACAAATGCATCAGAGGACAAGCTGAAAACTTTAAACCAAGTT
GGTACTGTTTAAAATATAAAGGAAATAGGTTTTTCAGGGAGCAAAGAGCT
ATTTCTGAGATTTGTTAAGGGTCAAGATACTTTGTTAAAACAGTGGAAGC
TGAGTCGGGGGTAATTTTTATCAGATAAAGGACTTCTTGGATTCTGTAAG
```

```
TTGCCTGTTCACTCTGATGGTAGTTTCTTTTGCTCTGCAGAAGCTCTTTA

GTTTAATTAGATCCCATTTGTCAATTTTGGCTTTTGTTGCCATTGCTTTT

GGTGTTTTAGACATGAAGTCCTTGCCCATGCCTATGTCCTGAATGGTATT

GCCTAGGTTTTCTTCTAGGGTTTTTATGGTTTTAGGTCTAACATTTAAGT

TTTTAATCCATCTTGAATTAATTTTTGTATAACGTGTAAGGAAGGGATCC

AGTTTCAGCTTTCTACATATGGCTAGCCAGGTTTCCCAGCACCGTTTGTT

GGGAATTGAACAATGAAAACACTTGGACACAGGAAGGCGAACATCACACA

CCGGGGCCTGTTGTCAGGTGGCGGGAGTGGGGAGGGATAGCATTAGGACA

TATACCTAATGTAAATGACGAGTTAATAGGTGCAGCACACCGACATGGCA

CATGTATACACATGTAACAAACATGCACATTGTGCACATGTACCCTAGAA

CTTAAAGTATAATAAAAAAATATATATACATATACATATATATATGTATA

TGTATATATATAAAAGGACTTCTTGAAAGGATGGTCCCTGCGTGGCTTAG

GTAAGTGGCAGCAAGGCTGGCTAGCCAGGCTTAGGAATCTAGGACATGCC

ACAGGACCCCTGATGGGTGGGTGGCTGCGGCTGCCAGAACAGGACCCTGG

ATGTGGCTACTGGCATTGCTGCCATCATTGCTGGAATGAATTAGATACTG

TCCTGCTTCAGAGTGCGCAGGCCCAGGCCCAGAAGAAAGCTTCTGATTGG

CCCAGCATGGCTCAGCTCCACCAGGACACAGTTTGGGCGCCTCAGCTGAC

CTCACAATGCAAGGCAGGGCTGCCTCCCACCCAGCTCACAAACGTGGTCT

CAGATGTTGGGTATCCCCCATGCCCCCGCCAAAAGCACTCCAGATGACAA

AAATCCACTACAAAGCTCTTCTTTAAAAAGAAAGATTCTGAGAAGTTCCA

TCAAAAGAAGAAAAGAAGAAATGAAGGTGATTGATCACCATATTTGCTTT
```

The nucleotide sequence of SEQ ID NO: 7 is part of GeneBank Accession No. AY438641, which is hereby incorporated by reference in its entirety.

The promoter of SEQ ID NO: 8 has the following nucleotide sequence:

```
GCATGTCTGTCTCTGTGTCCAAATTTTCCCTTTTTAAAAAGGCACTAGCC

ATAATGGATTAGGGTTCACCATAATGAGTTCATTTTAACTAAACAAATTA

CCTCTATAAACACCCTGTCTCCAAATAAGGTCACATTCTCTGGTACTGGG

GATTGGGACTTCAATGTATGAGTGTTTTGGGGCACACCAGTTAGCCCGTA

ACAGGGTAGCTGCAATGATGACAGGAAATCAGGGATGGGTAAGCATTCAT

AAATGTCACTCTCCTAGAGGAAAGGGAGGCTTCCTTTCGGGGACATTTTT

TGTCCTCATCTTGCCTGGGTTATAGAAGCAACTCACATAGGATTTTTGCT

GGGTGACTCCCTACCCTACTGCAGATGATTCCACTGTACACTCTGGGAGG

GACATGTGCTGTAAACTCAGCATAAAATGTCATAGTGGTCCCAACTCAGC

ATAAAATGTCATAGGGCACCCCGGCTGGGTGAATTCTTCCAGACCCTGTT

TTCTCTTCCTCATGCTTCAGACCTCTTCATTTCACAAGCAGTCTGTTGAA

GTAACCAAACTCCCAGGCCCAGAGTCAGCCAATCTGCATTTCAACCCCCC

ACCTCCATTCCTCAGCAATGGCCCTTCATCTTGGAAATCAGAATTAATCA

CAGCCTCTATGCCTGAATTAAAGTTTGCTCTTGTATCTTCTTTACCAACT

TTACATATACTCAATATTGGTGTATACAACTATGTAATGCAGTATGACCT

CTCTCTGTCTCTGTTCTCCTGGCAACTCATTCAGGCTCCATTCCCTTCAT

ATCCCACTTGAATTTGCACTACTCTGCACCACTGACTTTAGAATCTGTCT

TGTAAATAGGGTCAGAGTTCCTCAGCCAGATCCCGATGGGTAAAAGGAAC

CATGTCCCCACCCTGAGTTGAGCAGGTCTTCAAGAAACCCTCTTGTGAGT

CCACTCTGCCCCAAAGCTGCCTCCCAAAGATGCAGCATCTGTCCTGGCAG

AGTGTGGGCAGGAAGGCTGCCTTGCCAGGCTCCTGACTCCCAGTGCTGCG

TGGTGCTGATGAGCTGAGCTGATCTTTGAGGGGCCAGACCAGGTGAAAGT

TCCCACCCTAAGCAGCTCAGGGCAGGGACAGACCAAATCCAAGTGCACCA

AATGGGGCCATGAGAAACCCTCCTGTGGGGATATCTGTGATCTCAGGAAT

GACCCTGAGAGGACACTGCTCTGATGCTCTGATGAGACTGAGGGGGATTC

CAAGCTTCCAGGGTGCTGGGCAGTGTCTCCCCAGAGAGTGGCTGTTCCCA

GTGTCAATCAGGCAGGAAGGGTAGAATGCTGGGACAGGAAGTAGCTTGGA

GGTGGGCCTTAGGCTGGTAGAAGTTGCTGCTTTCTTCTCTGTGGGCTCCT

TTCTCGTGGATCTGGACCCCAGGAGTTCCCAGGCATAGAGAGGAGGGGTG

CCAGGTGATGGGGTGATGGAGGCGGTGGCCACGGCCCTGGAGAAGGCTG
```

The nucleotide sequence of SEQ ID NO: 8 is part of GeneBank Accession No. AY438640, which is hereby incorporated by reference in its entirety.

Another aspect of the present invention is directed to an isolated nucleic acid construct which includes a promoter which functions only in stem cells, a nucleic acid encoding a protein, and a 3' control region. The promoter, the nucleic acid encoding a protein, and the 3' control region are positioned with respect to one another to permit expression of protein, where the promoter has a nucleotide sequence selected from the group consisting of SEQ ID NO: 4, SEQ ID NO: 5, SEQ ID NO: 6, SEQ ID NO: 7, and SEQ ID NO: 8. Expression vectors, host cells, and transgenic animals containing this nucleic acid construct are also disclosed.

The present invention further relates to a method of isolating stem cells from a mixed population of different cell types. This method involves selecting a promoter which functions only in said stem cells and not in the other cell types. The promoter can have a nucleotide sequence selected from the group consisting of SEQ ID NO: 4, SEQ ID NO: 5, SEQ ID NO: 6, SEQ ID NO: 7, and SEQ ID NO: 8. A nucleic acid molecule encoding a marker protein under control of said promoter is introduced into all cell types of said mixed population and only the stem cells, but not the other cell types, within said mixed population are allowed to express said marker protein. The cells of said mixed population of cell types that are expressing the marker protein, which are restricted to the stem cells are identified and separated from the mixed population, where the separated cells are restricted to the stem cells.

Using the promoter of the present invention, a nucleic acid molecule encoding a protein marker, preferably a fluorescent protein under the control of the promoter is introduced into a plurality of cells to be sorted.

A green fluorescent protein is particularly useful in accordance with the present invention. An isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., 1992; U.S. Pat. No. 5,491,084). A mutated form of this GFP (a red-shifted mutant form) designated pRSGFP-C1 is commercially available from Clontech Laboratories, Inc. (Palo Alto, Calif.).

Other forms of suitable fluorescent proteins are described below.

AsRed2, a variant of *Anemonia sulcata* red fluorescent protein. AsRed2 has been engineered for brighter fluorescence. The AsRed2 coding sequence contains a series of silent base-pair changes, which correspond to human codon-usage preferences for optimal expression in mammalian cells.

AmCyan is a variant of wild-type *Anemonia majano* cyan fluorescent protein that has been engineered for brighter fluorescence.

DsRed, a novel red fluorescent protein (excitation maximum=558 nm; emission maximum=583 nm), was originally isolated from an IndoPacific sea anemone-relative, *Discosoma* sp.

pEBFP carries a blue fluorescent variant of the *Aequorea victoria* green fluorescent protein gene. The EBFP gene contains four amino acid substitutions. The Tyr-66 to His substitution gives EBFP fluorescence excitation and emission maxima (380 and 440 nm, respectively) similar to other blue emission variants.

pECFP encodes an enhanced cyan fluorescent variant of the *Aequorea victoria* green fluorescent protein gene. The ECFP gene contains six amino acid substitutions. The Tyr-66 to Trp substitution gives ECFP fluorescence excitation (major peak at 433 nm and a minor peak at 453 nm) and emission (major peak at 475 nm and a minor peak at 501 nm) similar to other cyan emission variants.

pEYFP encodes an enhanced yellow-green variant of the *Aequorea victoria* green fluorescent protein (GFP). The EYFP gene contains the four amino acid substitutions previously published as GFP-10C.

See BD Biosciences for further information on fluorescent proteins.

Standard techniques are then used to place the nucleic acid molecule encoding the protein under the control of the chosen cell specific promoter. Generally, this involves the use of restriction enzymes and ligation.

The resulting construct, which comprises the nucleic acid molecule encoding the protein under the control of the selected promoter (itself a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses and lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual*, Cold Springs Laboratory, Cold Springs Harbor, N.Y. (1989), which is hereby incorporated by reference in its entirety.

In accordance with one of the above-described methods, the nucleic acid molecule encoding the GFP is thus introduced into a plurality of cells. The promoter which controls expression of the GFP, however, only functions in the cell of interest. Therefore, the GFP is only expressed in stem cells. Since GFP is a fluorescent protein, the stem cells of interest can therefore be identified from among the plurality of cells by the fluorescence of the GFP.

Any suitable means of detecting the fluorescent cells can be used. The cells may be identified using epifluorescence optics, and can be physically picked up and brought together by Laser Tweezers (Cell Robotics Inc., Albuquerque, N.Mex). They can be separated in bulk through fluorescence activated cell sorting, a method that effectively separates the fluorescent cells from the non-fluorescent cells.

The present invention also relates to a population of cell types enriched in stem cells. All cell types in the population contain a promoter which functions only in said stem cells and has a nucleotide sequence selected from the group consisting of SEQ ID NO: 4, SEQ ID NO: 5, SEQ ID NO: 6, SEQ ID NO: 7, and SEQ ID NO: 8. The stem cells may be totipotent or pluripotent and are preferably derived from humans. Such stem cells are useful in replacing cardiomyocytes lost as a result of myocardial infarction. Additionally, these stem cells are useful in generation of vasculature in ischemic cardiac tissue.

Another aspect of the present invention is directed to an isolated nucleic acid construct which includes a promoter which functions only in stem cells, a nucleic acid encoding a protein, and a 3' control region. The promoter, the nucleic acid encoding a protein, and the 3' control region are positioned with respect to one another to permit expression of the protein, where the promoter has a nucleotide sequence selected from the group consisting of SEQ ID NO: 4, SEQ ID NO: 5, SEQ ID NO: 6, SEQ ID NO: 7, and SEQ ID NO: 8. Expression vectors, host cells, and transgenic animals containing this nucleic acid construct are also disclosed.

The present invention is also directed to a method of monitoring stem cell movement in a transgenic animal. This method involves providing a transgenic animal containing the above described nucleic acid construct and identifying locations in the transgenic animal which express the marker protein at different periods of time. The locations identified correspond to where stem cells are located at the different periods of time. The transgenic animal can be a human, mouse, rat, goat, cow, or pig.

Yet another embodiment of the present invention relates to a method of treating a patient having a disorder mediated by cell proliferation. This is carried out by administering to the patient a nucleic acid construct comprising a promoter which functions only in stem cells and a nucleic acid encoding an enzyme capable of converting a prodrug to a cytotoxic drug. The promoter has a nucleotide sequence selected from the group consisting of SEQ ID NO: 4, SEQ ID NO: 5, SEQ ID NO: 6, SEQ ID NO: 7, and SEQ ID NO: 8. The prodrug is also administered to the patient. This method is carried out under conditions effective for the enzyme to be expressed and to convert the prodrug to the cytotoxic drug so that the disorder mediated by cell proliferation is treated.

This method of treatment employs what is known as "suicide" gene strategy. Suicide gene therapy approaches using deactivated drugs are known as gene-directed enzyme prodrug therapy (GDEPT).

GDEPT is a two-step treatment. In the first step, a gene encoding a foreign enzyme is delivered to the patient (e.g., at a tumor) for expression. Second, a prodrug is administered that can be converted to a cytotoxic drug by the enzyme that has been expressed in the tumor. The foreign enzyme needs to be expressed exclusively in tumor cells, which could be achieved by controlling the expression of the enzyme with the above-described promoters of the present invention. The cytosine deaminase 5-fluorocytosine (CD-5-FC) system has been extensively investigated. In this system, non-toxic 5-fluorocytosine ("5-FC") is used as a substrate for cytosine deaminase (CD), which converts 5-FC into toxic 5-fluorouracil (5-FU). The CD-5-FC system, with expression of CD under control of one of the promoters of the present invention, can be administered to cells by any of the above-described techniques, including viral-mediated administration. Other suitable enzymes include herpes simplex virus thymidine kinase, and other suitable prodrugs include ganciclovir. See Denny W A. "Prodrugs for Gene-Directed Enzyme-Prodrug Therapy (Suicide Gene Therapy)," *J Biomed Biotechnol.* 2003(1):48-70 (2003); Yazawa K, et. al., "Current Progress in Suicide Gene Therapy for Cancer," *World J Surg.* 26(7):783-9(2002); Kim D, et. al., "The Emerging Fields of Suicide Gene Therapy and Virotherapy," *Trends Mol Med.* 8(4 Suppl): S68-73 (2002), which are hereby incorporated by reference in their entirety.

The disorder mediated by cell proliferation can be rheumatoid arthritis, lupus, type 1 diabetes, multiple sclerosis, cancer, restenosis (e.g., artificial vascular restenosis), gout, or other proliferative diseases involving abnormal cellular proliferation. It is particularly preferred that the disorder be a human disorder mediated by cell proliferation.

EXAMPLES

Example 1

Database Searches and Computer Analysis

Analysis of nucleotide sequences was performed using the National Center for Biotechnology Information and the Celera Discovery System. Potential transcription factor binding sites were mapped to putative AC133 promoters using the AliBaba softwar and TFsearch.

Example 2

Cell Culture

All cell lines for this study were obtained from ATCC (American Type Culture Collection, Manassas, Va.). Human retinoblastoma cell line WERI-Rb-1 and human teratocarcinoma cell line NTERA-2 cl.D1 (NT-2) were grown in Dulbecco's Modified Eagles Medium, supplemented with 10% fetal bovine serum. Colon cancer cell line Caco-2 was grown in Eagle's Minimum Essential Medium supplemented with 20% fetal bovine serum. All media were supplemented with 2 mM L-glutamine, 100 units/ml penicillin, 100 mg/ml streptomycin and 0.25 μg/ml fungizone (BioWhittaker, Walkersville, Md.).

Example 3

Isolation of CD34+Cells From Cord Blood

Human cord blood samples were obtained in conjunction with ethical and biohazard guidelines set by the institution. CD34+cells were purified by magnetic activated cell sorting columns (MACS, Miltenyi Biotech, Auburn, Calif.) using microbead conjugated antibodies. Two purification cycles were performed using separate columns. The purity of each batch of CD34+selected cells was determined by flow cytometry using fluorescein isothiocyanate (FITC, green fluorescence)-labeled anti-CD34 monoclonal antibodies(mAbs, Miltenyi Biotech).

Example 4

Rapid Amplification of cDNA Ends (RACE)

In order to perform 5'-RACE for AC133 on Caco-2 cells, NT-2 cells, and CD34+cells isolated from cord blood, total RNA was isolated using Concert Cytoplasmic RNA Isolation Reagent (Invitrogen Corporation, Carlsbad, Calif.). RACE ready cDNA was prepared using GeneRacer RLM Racer Kit (Invitrogen Corporation, Carlsbad, Calif.) according to the manufacturer's protocol. 5'-RACE on human brain, kidney and testis cDNA was performed using RLM-5'-RACE ready brain, kidney, and testis cDNA (Invitrogen Corporation, Carlsbad, Calif.) according to the manufacturer's protocol. All 5'-RACE experiments were carried out using two AC133 specific primers matching sequences in exon 2: 5'-GAG-GCATCAGAATAATAAACAGCAGC-3' (SEQ ID NO: 9) and nested 5'-CAGCAGCAACAGGGAGCCGAGTA-3' (SEQ ID NO: 10), and Platinum Taq DNA Polymerase High Fidelity (Invitrogen Corporation, Carlsbad, Calif.). Resulting PCR products were purified, cloned into the pCR4-TOPO vector (Invitrogen Corporation, Carlsbad, Calif.) and sequenced.

Example 5

Northern Hybridization Analysis

A fragment of AC133 cDNA (361 bp) common to all known isoforms was amplified by RT-PCR, using AC133 specific primers: 5'-CTAGATACTGCTGTTGATGTC-3' (SEQ ID NO: 11) and 5'-CTGCTCTAGGTTGACACACTT-3' (SEQ ID NO: 12), cloned into pBlueScript KS-(Stratagene, La Jolla, Calif.), and the digested fragment was used as a probe for AC133 detection on a Northern blot. As an internal control for loading, a fragment of G3PDH (408 bp) was amplified by RT-PCR, using G3DPH specific primers: 5'-CCCATCACCATCTTCCAGGAG-3' (SEQ ID NO: 13) and 5'-AGGGATGATGTTCTGGAGAGCC-3' (SEQ ID NO: 14), cloned into pCR4-TOPO with a digested fragment used as a probe for G3DPH detection on a Northern blot. 20 μg of total RNA from Caco-2, WERI-Rb-1, and NT-2 cell lines was resolved on a 1.2% formaldehyde agarose gel, transferred to Nytran SuPerCharge (Schleicher&Schuell Inc., Keene, N.H.), and probed with a $^{32}$P-labeled probe.

Example 6

RT-PCR Analysis

Human MTC Panel I, Human MTC Panel II, and Human Immune System MTC Panel (Clontech, Palo Alto, Calif.) were used as a source of cDNA from 18 human tissues for RT-PCR. Amplification was performed using forward primers 5'-GTCCAATCAGAGTGCGTCCA-3' (SEQ ID NO: 15) and nested 5'-GGCCATGCTCTCAGCTCT-3' (SEQ ID NO: 16) for exon 1A, 5'-GCGGCAGCGGTGACTA-3' (SEQ ID NO: 17) and nested 5'-GAGCAGGAGCGGGAGC-3' (SEQ ID NO: 18) for exon 1B, 5'-GAACTGCGGGGAGAGCGT-3' (SEQ ID NO: 19) and nested 5'-CGGAGCGGGAGTCGGA-3' (SEQ ID NO: 20) for exon 1C, 5'-CCAAAAGCACTCCA-GATGACA-3' (SEQ ID NO: 21) and nested 5'-AATCCAC-TACAAAGCTCTTC-3' (SEQ ID NO: 22) for exon 1D1, 5'-TTCTTCTCTGTGGGCTCCT-3' (SEQ ID NO: 23) and nested 5'-CTTTCTCGTGGATCTGGAC-3' (SEQ ID NO: 24) for exon 1E1, and two reverse primers located in common exon 2 of AC133: 5'-TCTTGGGTCTCATAATTTGTTG-CAGGC-3' (SEQ ID NO: 25) and nested primer 5'-TTCCCG-CACAGCCCCAGCAGCAACAG-3' (SEQ ID NO: 26). PCR was performed using Advantage 2 Taq Polymerase (Clontech, Palo Alto, Calif.). PCR conditions were as follows: 94° C. for 1 min followed by 25 cycles (first round) or 32 cycles (second round with nested primers) of 94° C. for 30 sec, 60° C. for 30 sec and 72° C. for 30 sec. RT-PCR on Caco-2, NT-2, brain, kidney, and CD34+human cord blood cell RACE-ready cDNA was performed as indicated above, with one exception: a 5'-RACE outer adapter primer was used instead of gene specific primers for exons 1A, 1B, 1C, 1D, and 1E in the first round of PCR.

Example 7

Construction of Luciferase Reporter Vectors

The BAC clone RP 11-452J21, containing exons 1A, 1B, 1C, exons of 1D and 1E clusters and exons 2 and 3 of AC133 and their flanking regions, was obtained from Research Genetics (Invitrogen Corporation, Carlsbad, Calif.). All promoter fragments were generated by PCR using primers to different regions of AC133 P1, P2, P3, P4 and P5 (Table 1).

TABLE 1

| Construct | Forward primer (with Kpn I site) | Reverse primer (with Hind III site) |
|---|---|---|
| P1 (−1800/+10) | 5'-TGAGGTACCTTCAGTGCCTCTTTCAGT-3' (SEQ ID NO: 27) | 5'-CTTGAAGCTTGTGGGGATCTGCCTCAGTCA-3' (SEQ ID NO: 28) |
| P1 (−1100/+10) | 5'-TGAGGTACCTATCCTGAGAACTCACTCACTA-3' (SEQ ID NO: 29) | 5'-CTTGAAGCTTGTGGGGATCTGCCTCAGTCA-3' (SEQ ID NO: 28) |
| P1 (−750/+10) | 5'-TGAGGTACCTTTGTAGCTTGTGCATCCAT-3' (SEQ ID NO: 30) | 5'-CTTGAAGCTTGTGGGGATCTGCCTCAGTCA-3' (SEQ ID NO: 28) |
| P1 (−490/+10) | 5'-TGAGGTACCACAGAGCGGGAAGACCAA-3' (SEQ ID NO: 31) | 5'-CTTGAAGCTTGTGGGGATCTGCCTCAGTCA-3' (SEQ ID NO: 28) |
| P1 (−349/+10) | 5'-CTAGGTACCTGCACACTAAGGATCCAAAT-3' (SEQ ID NO: 32) | 5'-CTTGAAGCTTGTGGGGATCTGCCTCAGTCA-3' (SEQ ID NO: 28) |
| P1 (−750/−250) | 5'-TGAGGTACCTTTGTAGCTTGTGCATCCAT-3' (SEQ ID NO: 29) | 5'-AGTAAGCTTACCCTTCTGTTGCCTAATC-3' (SEQ ID NO: 33) |

TABLE 1-continued

| Construct | Forward primer (with Kpn I site) | Reverse primer (with Hind III site) |
|---|---|---|
| P1 (−490/−250) | 5'-TGAGGTACCACAGAGCGGGAAGACCAA-3' (SEQ ID NO: 34) | 5'-AGTAAGCTTACCCTTCTGTTGCCTAATC-3' (SEQ ID NO: 35) |
| P2 | 5'-ACTGGTACCGGTCCAATCAGAGTGCGT-3' (SEQ ID NO: 36) | 5'-ATGAAGCTTCCCTTAGCTCGCCAGA-3' (SEQ ID NO: 37) |
| P3 | 5'-ACTGGTACCGGCGGCAGCGGTGACTA-3' (SEQ ID NO: 38) | 5'-ACTAAGCTTGCACACTCACCTCCGACT-3' (SEQ ID NO: 39) |
| P4 | 5'-ACTGGTACCGACAGACCCCAGATAGCCT-3' (SEQ ID NO: 40) | 5'-ACTAAGCTTAGCCTGGGTGACAGAGACT-3' (SEQ ID NO: 41) |
| P5 | 5'-ACTGGTACCGCATGTCTGTCTCTGTGTCC-3' (SEQ ID NO: 42) | 5'-ACTAAGCTTACTGACAACTGCCCACTGC-3' (SEQ ID NO: 43) |

All primers contained 5'-adapters with restriction sites for Kpn I or Hind III. Amplified fragments were double digested with Kpn I and Hind III and cloned into Kpn I/Hind III sites of the pGL3-Enhancer firefly luciferase vector (Promega Corporation, Madison, Wis.). Plasmids were purified using the HiSpeed Plasmid Midi Kit (QIAGEN Inc, Valencia, Calif.) and verified by sequencing.

Example 8

Transient Transfections and Luciferase Assays

All pGL3 and Renilla Luciferase vectors were obtained from Promega (Promega Corporation, Madison, Wis.). All transfections were carried out in 6-well plates (Corning Inc., Corning, N.Y.). Cells were plated 24 hours prior to transfection at a density of $2 \times 10^5$ per well, and transfections were carried out in antibiotic free medium. 1.5 µpg of reporter construct in pGL3-Enhancer vector and 30 ng of Renilla Luciferase-Null vector (as an internal control for transfection efficiency) were transfected, using 3 µl of Lipofectamine 2000 Transfection Reagent (Invitrogen Corporation, Carlsbad, Calif.) according to the manufacturer's protocol. 48 hours after transfection, cells were washed with phosphate-buffered saline and lysed with 500 µl of Passive Lysis Buffer (Promega Corporation, Madison, Wis.). Activities of firefly and Renilla luciferases were measured with a TD-20/20 Luminometer (Turner Designs, Sunnyvale, Calif.) using the Dual Luciferase Reporter Assay System (Promega Corporation, Madison, Wis.) according to the manufacturer's protocol. Firefly luciferase activity was normalized by Renilla luciferase activity. pGL3-Enhancer (promoter-less) vector was used in all experiments as a negative control and as a baseline for data comparisons. pGL3-Control (contains SV40 promoter and SV40 enhancer) vector was used in all experiments as a positive control.

Example 9

In Vitro DNA Methylation

Plasmid DNA (20 µg) was incubated without (mock methylated) or with (methylated) 20 units of SssI methylase (New England BioLabs, Inc., Beverly, Mass.) at 37° C. for 24 hours, supplemented every four hours with 160 µM S-adenosylmethyonine. Complete methylation at CpG sites was confirmed by Hpa II digestion of plasmid DNA. Before transfection, methylated DNA was purified using the Wizard DNA Clean-Up System (Promega Corporation, Madison, Wis.). Data from methylated and mock methylated constructs were normalized by the activity of methylated or mock methylated pGL3-Enhancer plasmids, respectively.

Example 10

Determination of Transcription Start Point

Comprehensive analysis of pre-existing sequences of cDNA and ESTs for AC133 using NCBI databases revealed the presence of an additional exon (assigned as exon 1A) in the 5'-UTR of the AC133 transcripts upstream of the previously reported first exon (assigned as exon 2). Matching the nucleotide sequence of exon 1A to human genomic DNA showed that this exon is located ~8 Kb upstream of exon 2 (FIG. 1). All together, eight (four ESTs and four cDNA) sequences containing exon 1A were found in the database. Positioning of the first nucleotide of those eight sequences to genomic DNA did not reveal a precise transcription start point. One group of two sequences and another group of three sequences were found with the same transcription start point, while three other sequences contain different start points. Unexpectedly, one EST derived from skeletal muscle did not show any homology with exon 1A, instead showing homology to a region of genomic DNA ~500 bp downstream of exon 1A. This datum indicates the possibility of an alternative first exon (assigned as a putative exon 1 C).

5'-RACE was performed in order to map the transcription start point for AC133 transcripts. Commercial RACE-ready cDNA and nested primers located in exon 2 to perform 5'-RACE on human, kidney, brain and testis cDNA were used. RACE fragments were subcloned into pCR4-TOPO vector and sixty four clones were sequenced. Several alternative variants of the 5'-terminal sequences were found. Two bands from the kidney sample were detected, isolated, and sequenced (FIG. 1B). Sequence analysis revealed that the lower, more abundant band contained predominantly sequences corresponding to exon 1A, and trace amounts of DNA corresponding to a novel sequence matching a 60 bp segment of genomic DNA ~250 bp downstream of exon 1A and 200 bp upstream of putative exon 1C. This novel alternative first exon was assigned to be exon 1B (FIG. 1A). Analysis of upper band revealed a match to exon 1A, with an alternative transcription initiation point 55 bp longer than the sequence derived from the lower band. Only one band was detected in the brain sample, which matched exon 1 B (FIG. 1B).

Multiple bands were found in the testis 5'-RACE product (FIG. 1C). Analysis revealed two clusters of 5'-UTR exons.

The first cluster, named 1D, was found ~3 Kb downstream of exon 1C and ~4 Kb upstream of exon 2. It contained three exons (D1, D2 and D3), which form at least three 5'-UTR alternatively spliced isoforms, differing from one another by inclusion of D2 and/or D3 (FIG. 1 A). The second cluster, named 1E, contained four exons (E1, E2, E3 and E4), 36 Kb upstream of exon 1A. Exons from cluster 1E generate at least two new alternatively spliced forms, differing from each other by the presence or absence of exon E2 (FIG. 1A). All newly discovered exons are spliced according to the GT-AG rule (Table 2).

TABLE 2

| Exon | 5' splice donor | | 3' splice acceptor | | Exon |
|---|---|---|---|---|---|
| 1A | CCGCGgtgagta | (SEQ ID NO: 44) | ctgccagGGATG | (SEQ ID NO: 45) | 2 |
| 1B | GCACGgtgagta | (SEQ ID NO: 46) | ctgccagGGATG | (SEQ ID NO: 45) | 2 |
| 1C | CGGAGgtgagtg | (SEQ ID NO: 47) | ctgccagGGATG | (SEQ ID NO: 45) | 2 |
| D1 | TGAAGgtgattg | (SEQ ID NO: 48) | acttcagAGGGA | (SEQ ID NO: 49) | D2 |
| D2 | CTGCGgtgagca | (SEQ ID NO: 50) | ctgagagGGAGG | (SEQ ID NO: 51) | D3 |
| D3 | AGATAgtaagtg | (SEQ ID NO: 52) | ctgccagGGATG | (SEQ ID NO: 53) | 2 |
| E1 | GCCAGgtgatgg | (SEQ ID NO: 54) | gccacagTGGAG | (SEQ ID NO: 55) | E2 |
| E2 | AACAGgtgtcaa | (SEQ ID NO: 56) | tcaacagTGCCA | (SEQ ID NO: 57) | E3 |
| E3 | GTCAGgtgagtc | (SEQ ID NO: 58) | ttcatagTTCTG | (SEQ ID NO: 59) | E4 |
| E4 | ACAAGgtgagag | (SEQ ID NO: 60) | ctgccagGGATG | (SEQ ID NO: 45) | 2 |

Determination of transcription start point from 5'-RACE data for exon 1A revealed the most common transcription initiation site, although additional initiation points were observed. No exon 1C containing transcripts, nor any other new alternative exons, were detected in the RACE experiments. The existence of five alternative first exons suggested the presence of five alternative promoters (FIG. 1) which were named P1 (upstream of exon 1A), P2 (upstream of exon 1B), P3 (upstream of exon 1C), P4 (upstream of exon 1D1), and P5 (upstream of putative exon 1E1).

Example 11

Expression of AC133 Isoforms in Human Tissues

Sequence specific forward primers were designed for each first exon (1A, 1B, 1C, 1D and 1E) and a reverse primer for common exon 2 to screen different cell types for the presence of alternatively spliced AC133 5'-UTR isoforms.

Expression of AC133 and its isoforms were investigated in commercially available cDNA panels for 18 different adult human tissues using RT-PCR (FIG. 2). All analyzed tissues, with the exception of peripheral blood leukocytes, were found positive for AC133 transcript. However, PCR analysis of 5'-UTR isoforms of AC133 revealed a tissue dependent expression pattern. Liver, kidney, pancreas, placenta, lung, spleen, and colon express both exon 1A and exon 1B containing transcripts, brain, ovary, and fetal liver express only the exon 1A containing isoform, and prostate and small intestine express only the exon 1B containing transcript. Exon 1D was detected only in testis. Interestingly, 1A, 1B, or 1D isoforms were not detected in heart, skeletal muscle, thymus, or bone marrow. Therefore, it is possible that other isoforms of AC133 5'-UTR may exist. Interestingly, the exon 1C and exon 1E containing isoform was not detected in any tested tissues, probably due low expression level.

Example 12

Expression of AC133 Isoforms on Human Cell Lines

In order to find a suitable AC133 expressing cell line to test promoter activity, previously reported AC133+cell lines NT-2, Caco-2 and WERI-Rb-1 (Miraglia et al., "A Novel Five-Transmembrane Hematopoietic Stem Cell Antigen: Isolation, Characterization, and Molecular Cloning," *Blood* 90:5013-5021 (1997) and Corbeil et al., "The Human AC133 Hematopoietic Stem Cell Antigen is Also Expressed in Epithelial Cells and Targeted to Plasma Membrane Protrusions," *J Biol Chem*. 275:5512-5520 (2000), which are hereby incorporated by reference in their entirety) were screened by Northern blot hybridization (FIG. 2C). It was confirmed that all three cell lines express the AC133 transcript, with the highest expression level found in WERI-Rb-1 cells. Caco-2 and NT-2 cells showed similar levels of AC133 expression.

5'-RACE was performed on AC133 expressing cell lines Caco-2 and NT-2. The 5'-RACE data indicate the presence of exon 1A and exon 1B containing AC133 transcripts in Caco-2 cells, and exon 1A containing transcripts in NT-2 cells.

Nested PCR amplification, using our specific primers on pre-amplified RACE-ready cDNA, was performed. These results indicated that NT-2 and Caco-2 cell lines utilize two alternatively spliced variants of AC133 transcripts: the 1A and 1B isoforms. Applying this method to RACE-ready kidney and brain cDNA confirmed our 5'-RACE results, showing both 1A and 1B transcripts for kidney and only 1B transcripts for brain.

Example 13

Expression of AC133 Isoforms on
CD34+hematopoietic Stem Cells

Previously published data shows that the majority of CD34+cells also express AC133. In order to investigate the expression of different AC133 isoforms on CD34+cells, human CD34+cells from cord blood and used them to generate a RACE-ready cDNA. The expression of AC133 5'-UTR isoforms on CD34+cells by RT-PCR using primers for 1A, 1B, 1C, 1D, and 1E isoforms. It was found that CD34+ hematopoietic stem cells express the exon 1A containing isoform of AC133. In order to check the expression of other possible 5'-UTR isoforms of AC133 on CD34+cells, 5'-RACE was performed. No new isoforms of AC133 were found in these cells.

Example 14

Isolation and Analysis of Genomic Clones

Blast search revealed a genomic BAC clone which contains exons 1A, 1B, 1C, exon 2, exon 3 and clusters of exons 1D and 1E. In order to clone the putative promoter region of AC133, this BAC clone was obtained and fragments corresponding to putative promoters were amplified, subcloned into the pGL3-Enhancer vector, and verified by sequencing. This set of constructs includes an 1,810 bp segment of genomic DNA upstream of exon 1A (promoter P1), a 365 bp segment upstream of exon 1B (promoter P2), a 501 bp segment upstream of exon 1C (promoter P3), a 1,648 bp segment upstream of exon 1D1 (promoter P4) and a 1,575 bp segment upstream of exon 1E1 (promoter P5).

Analysis of the promoter region revealed multiple binding sites for different transcription factors (FIG. 3). There were no TATA-boxes found in all AC133 promoters. Exons 1A, 1B and 1C, and also promoters P2, P3 and at least partially P1, are located within a CpG island.

Example 15

Transcriptional Activity of AC133 Promoters in NT-2 and Caco-2 Cell Lines

Transient transfection experiments were carried out on NT-2 and Caco-2 cell lines. Unfortunately, the WERI-Rb-1 cell line could not be tested due to difficulties with transfection. Tested AC133 P1 and P2 promoter constructs, normalized by Renilla luciferase activity, revealed elevated levels of firefly luciferase activity compared to baseline activity of promoter-less pGL3-Enhancer vector (FIG. 4A). No significant increase in luciferase activity could be detected for the P3, P4 or P5 promoter constructs. The promoter segment in the construct with the highest luciferase activity (−1100/+10 P1) was subcloned into the pGL3-Enhancer vector in the reverse orientation. No luciferase activity was observed for this construct. Several 5' and 3' deletions of P1 were constructed and cloned into pGL3-Enhancer vector, and their activity was assayed using the luciferase system (FIG. 4C).

Example 16

AC133 Promoter Activity is Methylation Sensitive

Figure 5:
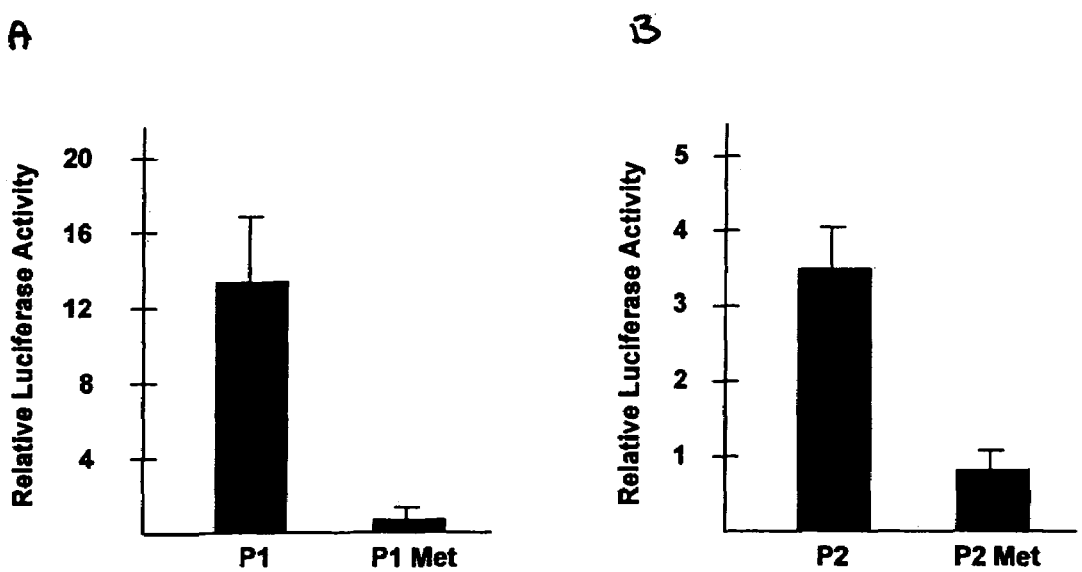
FIGS. 5A-B show the effect of in vitro methylation on the activity of human AC133 promoter. AC133 promoter 1 (–1100/+10) and promoter 2 luciferase constructs were mock methylated or methylated with SssI methylase. Both methylated and mock methylated constructs were transiently transfected into Caco-2 cell line, and luciferase activity was measured and normalized to the activity of the methylated and mock methylated pGL3-Enhancer vector respectively. All data represent the mean of three independent experiments.

The fact that the 5'-proximal region of the AC133 gene is located within a CpG island suggests a potential role of methylation in its transcriptional regulation. To examine the effect of methylation on AC133 promoter activity, P1 (−1100/+10) and P2 constructs were methylated with SssI methylase in vitro, and measured the luciferase activity of SssI methylated and mock methylated constructs. pGL3 Control plasmid, which contains the SV40 promoter, was both mock methylated and methylated and was included in the experiment as a negative control. Methylation completely suppresses the activity of AC133 promoters P1 and P2 in the Cacoc-2 cell line (FIG. 5).

In the present study, the AC133 (human prominin-1) 5'-UTR and promoter region were identified and characterized. It was shown that the structure of the human AC133 gene is more complex than was previously reported. Spanning over 152 Kb on chromosome 4, the AC133 gene contains at least 37 exons, with translation initiation sites positioned within exon 2 (previously assigned as exon 1). Four alternative AC133 promoters were also discovered, and the activity of two of them was demonstrated.

Recently, a novel alternatively spliced variant of human AC133, AC133-2, was reported (Yu et al., "AC133-2, a Novel Isoform of Human AC133 Stem Cell Antigen," *J Biol Chem* 277:20711-20716 (2002), which is hereby incorporated by reference in its entirety). This novel isoform lacks exon 4 (previously assigned as exon 3), which affects the AC133 ORF by deletion of 9 amino acids. Furthermore, it was shown that additional alternative splicing isoforms exist within the ORF of human AC133.

In addition, it was shown that AC133 transcripts can be alternatively spliced, resulting in the formation of mRNAs with different 5'-UTR exons. Nine distinct exons (1A, 1B, D1-3, E1-4) were found by 5'-RACE, and one additional exon (exon 1C) was discovered by analysis of ESTs for human AC133. The existence of at least seven alternatively spliced forms (A, B, D1, D1-D2, D1-D2-D3, E1-E3-E4 and E1-E2-E3-E4) was demonstrated (FIG. 1A). In agreement with these data, it was found that the mouse AC133 homolog prominin has four alternative 5'-UTR first exon. Furthermore, the data suggests that at least four promoters are involved in the transcriptional regulation of the AC133 gene. Although exon 1C containing transcripts could not be found in the analyzed tissues, and promoter P3 was not active in NT-2 and Caco-2 cell lines, it is possible that potential promoter P3 could still be involved in the transcriptional regulation of AC133 in other cell types. Exon clusters 1D and 1E were found exclusively in testis. It was not possible to detect these alternatively spliced forms neither in Caco-2 nor NT-2 cell lines. Activity of corresponding promoters P4 and P5 also could not be detected in these cell lines. Demonstration of their activity in a tissue specific manner should be a subject of future studies.

It was demonstrated that the AC133-2 transcript expression profile is different from that of the AC133-1 isoform and that the same organs may express different isoforms in fetuses and adults (Yu et al., "AC133-2, a Novel Isoform of Human AC133 Stem Cell Antigen," *J Biol Chem* 277:20711-20716 (2002), which is hereby incorporated by reference in its entirety). In addition, a tissue dependent pattern of expression of 1A, 1B and 1D containing isoforms of AC133 mRNA was found.

Regulation of certain genes by alternative promoters has previously been reported (Ayoubi et al., "Regulation of Gene Expression by Alternative Promoters," *FASEB J* 10:453-460 (1996), which is hereby incorporated by reference in its entirety). It is known that alternative non-coding leader exons may play a role in the regulation of the turnover or translation efficiency of mRNA isoforms (Ayoubi et al., "Regulation of Gene Expression by Alternative Promoters," *FASEB J* 10:453-460 (1996), which is hereby incorporated by reference in its entirety). It is believed that alternative AC133 promoters, through inclusion of different 5'-UTR, might also affect overall alternative splicing and cause the formation of specific isoforms of AC133 mRNA.

Assessment of AC133 promoter activity using luciferase reporter system revealed its relatively low activity without additional enhancer elements. A significant level of promoter activity could not be detected using pGL3-Basic vector, which contains neither SV40 promoter nor enhancer. Therefore, pGL3-Enhancer vector (containing SV40 enhancer) was used as a backbone for the reporter constructs in all studies. Consequently, it was suspected that additional regulatory elements play a crucial role in the proper functioning of the AC133 promoter.

AC133 first exons 1A, 1B and 1C and their promoters are found within a CpG island, suggesting that methylation plays a role in the regulation of AC133 transcriptional activity. The data showing the complete suppression of AC133 promoter activity in vitro with a methylated reporter construct in the luciferase test support this hypothesis. More extensive research should be performed to understand the importance of methylation in the regulation of AC133 expression in vivo.

Several cell lines, including NT-2 and Caco-2, were previously reported to be AC133 positive by FACS analysis (Miraglia et al., "A Novel Five-Transmembrane Hematopoietic Stem Cell Antigen: Isolation, Characterization, and Molecular Cloning," Blood 90:5013-5021 (1997) and Corbeil et al., "The Human AC133 Hematopoietic Stem Cell Antigen is Also Expressed in Epithelial Cells and Targeted to Plasma Membrane Protrusions," J Biol Chem. 275:5512-5520 (2000), which are hereby incorporated by reference in their entirety.) To identify a potential negative cell line for this promoter study, more than 20 cell lines were analyzed by RT-PCR and flow cytometry. Surprisingly, it was found that all cell lines were positive for AC133 by RT-PCR, even those which were negative by flow cytometry. In fact, using RT-PCR, AC133 expression was detected in most adult human tissues and cell types.

When discovered, the AC133 antigen was thought to be a hematopoietic stem cell specific marker. Indeed, the AC133 monoclonal antibody recognizes only a subpopulation of CD34+hematopoietic stem cells, and no immunoreactivity was found in other tissues, despite the detection of AC133 mRNA by RT-PCR and Northern blot (Miraglia et al., "A Novel Five-Transmembrane Hematopoietic Stem Cell Antigen: Isolation, Characterization, and Molecular Cloning," Blood 90:5013-5021 (1997) and Miraglia et al., "A Response to AC133 Hematopoietic Stem Cell Antigen: Human Homologue of Mouse Kidney Prominin or Distinct Member of a Novel Protein Family?," Blood 91:4390-4391 (1998), which are hereby incorporated by reference in their entirety). This finding could be explained by the fact that AC133 is a glycoprotein: it has been reported that the AC133 monoclonal antibody is glycosylation dependent, and glycosylation of the A133 protein may vary in different tissues (Yin et al., AC133, a Novel Marker for Human Hematopoietic Stem and Progenitor Cells," Blood 90:5002-5012 (1997), which is hereby incorporated by reference in its entirety).

However, there is another explanation for the discordance between antibody staining data and RT-PCR data. It is possible that the AC133 monoclonal antibody recognizes only one of the possible AC133 isoforms resulting from alternative splicing. The reported finding that the AC133 monoclonal antibody predominantly recognizes AC133-2 supports this hypothesis (Yu et al., "AC133-2, a Novel Isoform of Human AC133 Stem Cell Antigen," J Biol Chem 277:20711-20716 (2002), which is hereby incorporated by reference in its entirety). Previously, it was suggested that expression of AC133-2 or other isoforms of AC133 might be regulated by a particular alternative promoter. Thus, it is possible that only one of the alternative AC133 promoters regulates the transcription of a stem cell specific isoform.

It was shown that CD34+hematopoietic stem cells utilize only exon 1A containing AC133 mRNA isoforms. Therefore, AC133 promoter P1 may play a key role in the regulation of AC133 expression on CD34+cells. Considering this and the fact that expression of AC133 in hematopoietic system is restricted to CD34+cells, this finding will allow the fate of CD34+hematopoietic stem cells to be followed in vivo. Identification of a stem cell specific isoform of AC133 and its concurrent regulatory promoter will ultimately set the stage for the isolation of organ-specific stem cells (e.g., hematopoietic stem cells, vascular stem cells, endothelial stem cells, muscle stem cells, neural stem cells, cardiac stem cells) through the use of AC133 promoter reporter constructs.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. An isolated nucleic acid construct comprising:
   a promoter, wherein the promoter has a nucleotide sequence comprising nucleotides 1,778 through 2,888 of SEQ ID NO: 4;
   a nucleic acid encoding a protein selected from the group consisting of a reporter protein and an enzyme; and
   a 3' control region, wherein the promoter, the nucleic acid encoding a protein, and the 3' control region are positioned with respect to one another to permit expression of the protein.

2. The isolated nucleic acid construct of claim 1, wherein the promoter has a nucleotide sequence comprising nucleotides 1,078 through 2,888 of SEQ ID NO: 4.

3. The isolated nucleic acid construct of claim 1, wherein the promoter has the nucleotide sequence of SEQ ID NO: 4.

4. The isolated nucleic acid construct of claim 1, wherein the protein is a reporter protein.

5. The isolated nucleic acid construct of claim 4, wherein the reporter protein is a fluorescent protein.

6. An expression vector comprising the nucleic acid construct according to claim 1.

7. A host cell comprising the nucleic acid construct of claim 1.

8. The host cell of claim 7 wherein the nucleic acid construct is operatively positioned within an expression vector.

9. The isolated nucleic acid construct of claim 1, wherein the protein is an enzyme.

10. The isolated nucleic acid construct of claim 9, wherein the protein is an enzyme capable of converting a prodrug to a cytotoxic drug.

11. The isolated nucleic acid construct of claim 10, wherein the enzyme is selected from the group consisting of cytosine deaminase and herpes simplex virus thymidine kinase.

* * * * *

SEQUENCE LISTING

```
<160> NUMBER OF SEQ ID NOS: 60

<210> SEQ ID NO 1
<211> LENGTH: 2700
<212> TYPE: DNA
<213> ORGANISM: Artificial Sequence
<220> FEATURE:
<223> OTHER INFORMATION: Description of Artificial Sequence: promoter

<400> SEQUENCE: 1
tgcactctcc ctttcccaag ccacaaggct gctgctgctg ggggatggag gactggcggc        60
attggcaaat caaaactgtc tttcctggct tcttcagtgc ctctttcagt aatatgaaat       120
taaaaccagg tattgtggtt actcacctga tttttggttc ttataaaggt gcttttgtg        180 tgtgtagata gcagttaaat tgtgttccta gccgggtgg ggggtgggtg gtcaaacctt       240
ctatttgacc atcttgcttc acccctttct actgatacta ttgttgttga tattattagg       300
aatgaaaatg agccctgtga gttataattg tcttcatttt gcagaccagg aaactgaggc       360
```

```
tcagagaaat attaagcagc caaagtcaca gcgattaaaa gaggcgggac caaactttga    420
cggagatcag gacccactcc tttgagaaat cacctctttt gctagctcca gcctaaaagt    480
gctatctagg agaaggttta tgggacccca gcagatgttc aaccagaaac ttctgacctg    540
caggggctgc agaggggaaa tctgccctga ttagaagaga tttgttttcc acccatatta    600
gtttgatctc acattgctat aaagaactac ctgagactgg gtttcagagg ctgtaccgta    660
ggcatggcca gagaggcttc aggaaactta caattatggt ggaagaaggg aaagcaagca    720
catcttcaca tggcagaagg agagacagag cgagcaaagg ggaagtgcca cacacttta    780 aatcatcaga tatcctgaga actcactcac tatcatgaga acagcaaggg agaaatccgc    840
cctcataatc caatcacctc ccactaggtc cctctcccag tgaattataa ttcaatatga    900
gatttggatg gggacacaga gccaaaccat ctaaccttgc catgtcctac tgtactttt    960 ggaagttttc tgaactaaca tttcttgtct agaaatatac acactcaaga tcaatctaac   1020
tattaaaaac aaaaaatgct tattttccag tacctgtttt atgttagatt ctggggtaaa   1080
aagaaaaagg tactgactta atgttcctgt ctatcattca tttgtagctt gtgcatccat   1140
cctttcatct gtctatccat atcacaaaca tgtattaaac acctgctgta tgctagacac   1200
catcctgaag gtgcatttct tccctaagtc ttttttttgc ctgccggaga gtacagtatt   1260
ctcaattcaa gataagaagt ggtgaataag agtgaagtgc aaattggtga ggacacttag   1320
acaccgagtg attacttctg acaggtttcc accactcagc taagtagcaa ggtgaagact   1380
ccgaggttga gttgtaactc acagagcggg aagaccaata ggcagtgaga aaagaagttg   1440
cagtggcttc acgttatagc agatgcctgt gtgtacacat gggagcgaat atggctttat   1500 gctgttttc aaccgcttca gccactagca ttggtactgc tgcacactaa ggatccaaat   1560
gattgttttt ttgttttttg ttttgtttg ttttgttttg ttttgtttta aattgcattg   1620
ggattaggca acagaagggt ctaatgcggc cgggatgaga caggagagtt tttaggaggg   1680
tagctgcatt ctaagtaagg gactctgcgg ggggaaaaga ggcgcaagcg ttgcaagaag   1740
ggagtgcagg gggttgagca ggcacctcta caggaaatgg atgctgtcca ggtgctggtg   1800
ggcgccccag ggctacgtgg cgaagcagct cagccggtcc aatcagagtg cgtccagggc   1860
tcgggtttcg cgatctttaa gtgactgagg cagatcccca cgcggcacct ggccatgctc   1920
tcagctctcc cgccgcggtg agtatgttta aggaatcctt tccattacgg cggccccata   1980
cctaggtccc cgtccgggac agaggaagcc gcaacgggtc cccccgggca cccgggcctt   2040
tctcctgcct cccgccacgt ccgagggtcc ggccgcagcg ccgcctgagc ccctccgcgg   2100
ccggcagtgg gaggcgggct ctccgaaagc cgtcgcggtg gtcccagaag ccgggtcata   2160
aataattcac gagccagggt ctggcgagct aagggaaggg cggcggcagc ggtgactagg   2220
gcgggagcag gagcgggagc cgggtgcacg gtgagtagct gggtcctcat cccggagcga   2280
gagaggcatc tgctgaccag gcgcggggct gagcgcactc cttccactgt actggggtg    2340 tacagtgagg agtggacggg ttcgctctgc gccccctta ccctagccat ctgcgccgcc    2400
tccctggccc ctcagcaggt ggtgcgggcc cggacagcgg ctggggccca gaggaactgc   2460
ggggagagcg tggtggtgcc ggtgcccgtc aacccaaac ttttagtct gagtggtggc    2520 ccgcgacgcc ccgcttgggt cttctttcca tccactgggg atggggcgg gggtgggggt   2580 agccggcggc cgtggttccg gagcgggagt cggaggtgag tgtgcgaact ggaccggggc   2640
cccagagact tcggactcgc tctcggggag aacggtgacc gaggtgagac tcgccagggt   2700
```

```
<210> SEQ ID NO 2
<211> LENGTH: 1600
<212> TYPE: DNA
<213> ORGANISM: Artificial Sequence
<220> FEATURE:
<223> OTHER INFORMATION: Description of Artificial Sequence:  promoter

<400> SEQUENCE: 2
gacagacccc agatagcctt ccagctgcgt gccaggtgct ttacctatta gatcgctagc      60
ctgcgaaccc tatgcgaaat cctcctttga cagaggagca aagaagggt tggagaattc     120
```

```
<210> SEQ ID NO 2
<211> LENGTH: 1600
<212> TYPE: DNA
<213> ORGANISM: Artificial Sequence
<220> FEATURE:
<223> OTHER INFORMATION: Description of Artificial Sequence:  promoter

<400> SEQUENCE: 2
gacagacccc agatagcctt ccagctgcgt gccaggtgct ttacctatta gatcgctagc      60
ctgcgaaccc tatgcgaaat cctcctttga cagaggagca aagaagggt tggagaattc     120 aaacaactgt catcttggca gagttagtaa gggggaccag agcccccta ctgttgctgt     180 tgtctgtcta ttcagcagtg cccttagtt tattcttgtt ttttttttca tgtgttccat     240
aatttttttc taaacttcct tctgatttct aaacttttct aaacttcttt ctgatttcta     300
aacttccttc tgatttttat acgagacagt ttctttgtgt tttagtacaa tgaggtgaac     360
aaatgcatca gaggacaagc tgaaaacttt aaaccaagtt ggtactgttt aaaatataaa     420
ggaaataggt ttttcaggga gcaaagagct atttctgaga tttgttaagg gtcaagatac     480
tttgttaaaa cagtggaagc tgagtcgggg gtaattttta tcagataaag gacttcttgg     540
attctgtaag ttgcctgttc actctgatgg tagtttcttt tgctctgcag aagctcttta     600
gtttaattag atcccatttg tcaattttgg cttttgttgc cattgctttt ggtgttttag     660
acatgaagtc cttgcccatg cctatgtcct gaatggtatt gcctaggttt tcttctaggg     720
tttttatggt tttaggtcta acatttaagt ttttaatcca tcttgaatta atttttgtat     780
aaggtgtaag aagggatcc agtttcagct ttctacatat ggctagccag gtttcccagc     840
accgtttgtt gggaattgaa caatgaaaac acttggacac aggaagggga acatcacaca     900
ccggggcctg ttgtcaggtg gcgggagtgg ggagggatag cattaggaca tatacctaat     960
gtaaatgacg agttaatagg tgcagcacac cgacatggca catgtataca catgtaacaa    1020
acatgcacat tgtgcacatg taccctagaa cttaaagtat aataaaaaaa tatatataca    1080
tatacatata tatatgtata tgtatatata taaaaggact tcttgaaagg atggtccctg    1140
ggtggcttag gtaagtggca gcaaggctgg ctagccaggc ttaggaatct aggacatgcc    1200
acaggacccc tgatgggtgg gtggctgcgg ctgccagaac aggaccctgg atgtggctac    1260
tggcattgct gccatcattg ctggaatgaa ttagatactg tcctgcttca gagtgcgcag    1320
gcccaggccc agaagaaagc ttctgattgg cccagcatgg ctcagctcca ccaggacaca    1380
gtttgggcgc ctcagctgac ctcacaatgc aaggcagggc tgcctcccac ccagctcaca    1440
aacgtggtct cagatgttgg gtatccccca tgcccccgcc aaaagcactc cagatgacaa    1500
aaatccacta caaagctctt cttaaaaag aaagattctg agaagttcca tcaaaagaag    1560
aaaagaagaa atgaaggtga ttgatcacca tatttgcttt                         1600

<210> SEQ ID NO 3
<211> LENGTH: 1500
<212> TYPE: DNA
<213> ORGANISM: Artificial Sequence
<220> FEATURE:
<223> OTHER INFORMATION: Description of Artificial Sequence:  promoter

<400> SEQUENCE: 3
gcatgtctgt ctctgtgtcc aaattttccc ttttttaaaaa ggcactagcc ataatggatt      60
agggttcacc ataatgagtt catttttaact aaacaaatta cctctataaa caccctgtct     120
ccaaataagg tcacattctc tggtactggg gattgggact tcaatgtatg agtgttttgg     180
```

```
ggcacaccag ttagcccgta acagggtagc tgcaatgatg acaggaaatc agggatgggt      240
aagcattcat aaatgtcact ctcctagagg aaagggaggc ttcctttcgg ggacattttt      300
tgtcctcatc ttgcctgggt tatagaagca actcacatag gattttgct gggtgactcc       360 ctaccctact gcagatgatt ccactgtaca ctctgggagg acatgtgct gtaaactcag       420 cataaaatgt catagtggtc ccaactcagc ataaaatgtc ataggcacc ccggctgggt       480 gaattcttcc agaccctgtt ttctcttcct catgcttcag acctcttcat ttcacaagca      540
gtctgttgaa gtaaccaaac tcccaggccc agagtcagcc aatctgcatt caaccccccc      600
acctccattc ctcagcaatg gcccttcatc ttggaaatca gaattaatca cagcctctat      660
gcctgaatta agtttgctc ttgtatcttc tttaccaagt ttacatatac tcaatattgg       720
tgtatacaac tatgtaatgc agtatgacct ctctctgtct ctgttctcct ggcaactcat      780
tcaggctcca ttcccttcat atcccacttg aatttgcact actctgcacc actgacttta      840
gaatctgtct tgtaaatagg gtcagagttc ctcagccaga tcccgatggg taaaaggaac      900
catgtcccca ccctgagttg agcaggtctt caagaaaccc tcttgtgagt ccactctgcc      960
ccaaagctgc ctcccaaaga tgcagcatct gtcctggcag agtgtgggca ggaaggctgc     1020
cttgccaggc tcctgactcc cagtgctgcg tggtgctgat gagctgagct gatctttgag     1080
gggccagacc aggtgaaagt tcccacccta agcagctcag gcagggaca gaccaaatcc      1140 aagtgcacca atggggcca tgagaaaccc tcctgtgggg atatctgtga tctcaggaat      1200
gaccctgaga ggacactgct ctgatgctct gatgagactg aggggattc caagcttcca      1260 gggtgctggg cagtgtctcc ccagagagtg gctgttccca gtgtcaatca ggcaggaagg     1320
gtagaatgct gggacaggaa gtagcttgga ggtgggcctt aggctggtag aagttgctgc     1380
tttcttctct gtgggctcct ttctcgtgga tctggacccc aggagttccc aggcatagag     1440
aggaggggtg ccaggtgatg ggggtgatgg aggcggtggc cacggccctg gagaaggctg     1500

<210> SEQ ID NO 4
<211> LENGTH: 2888
<212> TYPE: DNA
<213> ORGANISM: Artificial Sequence
<220> FEATURE:
<223> OTHER INFORMATION: Description of Artificial Sequence:  promoter

<400> SEQUENCE: 4
ggtacctaag gggaaggaaa acatcctctt tactttcct tctgcttttg tcaagcagaa        60
ggagtctctc acattagcca ccacagttgg gaatatactg ggtctcacct gaaaccagca      120
gatctcagag tcacacccaa gaaccacagt gtactacctg agtattgctt ctggctattg      180
agaacccaag ggctctttag ccaacaggtg atgggtcctg cccagactgt tctttccct       240 tcaaggcagc agtttccctt ctggcccagg atgtgtctag aaatgttatc cacaagttag      300
gacctgggat gggggtctga tgactcagac tgatgccctg tcctactgtg gctaaactga      360
tattcaagat aacaaagtcc tctttactct tcccctctt ctcttcaagc agaaggaatg       420
ggtctcttcg tgctgttttt aatcactcca gccactagca ttgggactga tgcagacact      480
aaggatccaa atgattattt ttgttttgtt tttttaactg cattgggatt aggcaacaga      540
agggtctaat gtgctgaga gttttgaga gaggagcatt tttaggaggg tagctgcatt        600
ccaagtagag agctctgctg gggtaaaaga ggcatgagtg ctagaaaagg gcatgcagtg      660
atgaagagcc actaacagca ctacctgggg ttggggtagg ggtgtcacaa gcactcccctt     720
```

-continued

```
agctcccctg tctggtgtct cagtaagtcg catgccctcc aagtctactg gctctgagct      780
cagcatttgg gcttgcttag gagttgctgt ccttgtggcc taggctgcct ttaaggttat      840
ttggggcccc agagcacttt actgaaactc aagttttcac cactggtatg ggctatttcc      900
tctgagggaa attggctgag ttcagcctag ttttgctttc tgctatgaca gagcagtact      960
gagttcaatt caaagtctcc caatcactgc actctcccctt tcccaagcca caaggctgct     1020
gctgctgggg gatggaggac tggcggcatt ggcaaatcaa aactgtcttt cctggcttct      1080
tcagtgcctc tttcagtaat atgaaattaa aaccaggtat tgtggttact cacctgattt      1140
ttggttctta taaggtgct ttttgtgtgt gtagatagca gttaaattgt gttcctagcc        1200
ggggtggggg gtgggtggtc aaaccttcta tttgaccatc ttgcttcacc cctttctact      1260
gatactattg ttgttgatat tattaggaat gaaaatgagc cctgtgagtt ataattgtct      1320
tcattttgca gaccaggaaa ctgaggctca gagaaatatt aagcagccaa agtcacagcg      1380
attaaaagag gcgggaccaa actttgacgg agatcaggac ccactccttt gagaaatcac      1440
ctcttttgct agctccagcc taaaagtgct atctaggaga aggtttatgg gaccccagca      1500
gatgttcaac cagaaacttc tgacctgcag gggctgcaga ggggaaatct gccctgatta      1560
gaagagattt gttttccacc catattagtt tgatctcaca ttgctataaa gaactacctg      1620
agactgggtt tcagaggctg taccgtaggc atggccagag aggcttcagg aaacttacaa      1680
ttatggtgga agaagggaaa gcaagcacat cttcacatgg cagaaggaga gacagagcga      1740
gcaaagggga agtgccacac acttttaaat catcagatat cctgagaact cactcactat      1800
catgagaaca gcaagggaga aatccgccct cataatccaa tcacctccca ctaggtccct      1860
ctcccagtga attataattc aatatgagat ttggatgggg acacagagcc aaaccatcta      1920
accttgccat gtcctactgt acttttttgga agttttctga actaacatttt cttgtctaga     1980 aatatacaca ctcaagatca atctaactat taaaaacaaa aaatgcttat tttccagtac      2040
ctgttttatg ttagattctg gggtaaaaag aaaaaggtac tgacttaatg ttcctgtcta      2100
tcattcattt gtagcttgtg catccatcct ttcatctgtc tatccatatc acaaacatgt      2160
attaaacacc tgctgtatgc tagacaccat cctgaaggtg catttcttcc ctaagtcttt      2220
tttttgcctg ccggagagta cagtattctc aattcaagat aagaagtggt gaataagagt      2280
gaagtgcaaa ttggtgagga cacttagaca ccgagtgatt acttctgaca ggtttccacc      2340
actcagctaa gtagcaaggt gaagactccg aggttgagtt gtaactcaca gagcgggaag      2400
accaataggc agtgagaaaa gaagttgcag tggcttcacg ttatagcaga tgcctgtgtg      2460
tacacatggg agcgaatatg gctttatgct gtttttcaac cgcttcagcc actagcattg      2520
gtactgctgc acactaagga tccaaatgat tgtttttttg tttttttgttt tgttttgttt     2580 tgttttgttt tgtttttaaat tgcattggga ttaggcaaca gaagggtcta atgcggccgg      2640
gatgagacag gagagtttt aggagggtag ctgcattcta agtaagggac tctgcggggg       2700
gaaaagaggc gcaagcgttg caagaaggga gtgcagggg ttgagcaggc acctctacag       2760
gaaatggatg ctgtccaggt gctggtgggc gccccagggc tacgtggcga agcagctcag      2820
ccggtccaat cagagtgcgt ccagggctcg ggtttcgcga tctttaagtg actgaggcag      2880
atccccac                                                              2888
```

<210> SEQ ID NO 5
<211> LENGTH: 365
<212> TYPE: DNA
<213> ORGANISM: Artificial Sequence

```
<220> FEATURE:
<223> OTHER INFORMATION: Description of Artificial Sequence: promoter

<400> SEQUENCE: 5
ccggtccaat cagagtgcgt ccagggctcg ggtttcgcga tctttaagtg actgaggcag      60
atccccacgc ggcacctggc catgctctca gctctcccgc cgcggtgagt atgtttaagg     120 aatccttttcc attacggcgg ccccataacct aggtccccgt ccgggacaga ggaagccgca   180
acgggtcccc ccgggcaccc gggcctttct cctgcctccc gccacgtccg agggtccggc    240
cgcagcgccg cctgagcccc tccgcggccg cagtgggag gcgggctctc cgaaagccgt    300
cgcggtggtc ccagaagccg ggtcataaat aattcacgag ccagggtctg gcgagctaag   360
ggaag                                                                 365

<210> SEQ ID NO 6
<211> LENGTH: 425
<212> TYPE: DNA
<213> ORGANISM: Artificial Sequence
<220> FEATURE:
<223> OTHER INFORMATION: Description of Artificial Sequence: promoter

<400> SEQUENCE: 6
cggcggcagc ggtgactagg gcgggagcag gagcgggagc cgggtgcacg gtgagtagct      60
gggtcctcat cccggagcga gagaggcatc tgctgaccag gcgcggggct gagcgcactc    120
cttccactgt actggggggtg tacagtgagg agtggacggg ttcgctctgc gccccctta    180 ccctagccat ctgcgccgcc tccctggccc ctcagcaggt ggtgcgggcc cggacagcgg   240 ctggggggcca gaggaactgc ggggagagcg tggtggtgcc ggtgcccgtc aacccaaac   300 ttttttagtct gagtggtggc ccgcgacgcc ccgcttgggg cttctttcca tccactgggg   360 atggggggcgg gggtgggggt agccggcggc cgtggttccg gagcgggagt cggaggtgag   420
tgtgc                                                                 425

<210> SEQ ID NO 7
<211> LENGTH: 1600
<212> TYPE: DNA
<213> ORGANISM: Artificial Sequence
<220> FEATURE:
<223> OTHER INFORMATION: Description of Artificial Sequence: promoter

<400> SEQUENCE: 7
gacagacccc agatagcctt ccagctgcgt gccaggtgct ttacctatta gatcgctagc      60
ctgcgaaccc tatgcgaaat cctcctttga cagaggagca aagaagggt tggagaattc     120 aaacaactgt catcttggca gagttagtaa gggggaccag agcccccttta ctgttgctgt   180 tgtctgtcta ttcagcagtg cccttttagtt tattcttgtt ttttttttca tgtgttccat    240 aattttttttc taaacttcct tctgatttct aaacttttct aaacttcttt ctgatttcta   300
aacttccttc tgatttttat acgagacagt ttctttgtgt tttagtacaa tgaggtgaac   360
aaatgcatca gaggacaagc tgaaaacttt aaaccaagtt ggtactgttt aaaatataaa   420
ggaaataggt ttttcaggga gcaaagagct atttctgaga tttgttaagg gtcaagatac   480
tttgttaaaa cagtggaagc tgagtcgggg gtaattttta tcagataaag gacttcttgg   540
attctgtaag ttgcctgttc actctgatgg tagtttcttt tgctctgcag aagctcttta    600
gtttaattag atcccatttg tcaatttggg cttttgttgc cattgctttt ggtgttttag   660
acatgaagtc cttgcccatg cctatgtcct gaatggtatt gcctaggttt tcttctaggg   720
```

-continued

```
ttttttatggt ttaggtctca acatttaagt ttttaatcca tcttgaatta attttttgtat      780 aaggtgtaag gaagggatcc agtttcagct ttctacatat ggctagccag gtttcccagc        840
accgtttgtt gggaattgaa caatgaaaac acttggacac aggaagggga acatcacaca        900
ccggggcctg ttgtcaggtg gcgggagtgg ggagggatag cattaggaca tatacctaat        960
gtaaatgacg agttaatagg tgcagcacac cgacatggca catgtataca catgtaacaa       1020
acatgcacat tgtgcacatg taccctagaa cttaaagtat aataaaaaaa tatatataca       1080
tatacatata tatatgtata tgtatatata taaaaggact tcttgaaagg atggtccctg       1140
ggtggcttag gtaagtggca gcaaggctgg ctagccaggc ttaggaatct aggacatgcc       1200
acaggacccc tgatgggtgg gtggctgcgg ctgccagaac aggaccctgg atgtggctac       1260
tggcattgct gccatcattg ctggaatgaa ttagatactg tcctgcttca gagtgcgcag       1320
gcccaggccc agaagaaagc ttctgattgg cccagcatgg ctcagctcca ccaggacaca       1380
gtttgggcgc tcagctgac ctcacaatgc aaggcagggc tgcctcccac ccagctcaca       1440
aacgtggtct cagatgttgg gtatccccca tgccccgcc aaaagcactc cagatgacaa       1500
aaatccacta caaagctctt ctttaaaaag aaagattctg agaagttcca tcaaaagaag       1560
aaaagaagaa atgaaggtga ttgatcacca tatttgcttt                              1600

<210> SEQ ID NO 8
<211> LENGTH: 1500
<212> TYPE: DNA
<213> ORGANISM: Artificial Sequence
<220> FEATURE:
<223> OTHER INFORMATION: Description of Artificial Sequence:  promoter

<400> SEQUENCE: 8
gcatgtctgt ctctgtgtcc aaattttccc tttttaaaaa ggcactagcc ataatggatt         60
agggttcacc ataatgagtt cattttaact aaacaaatta cctctataaa cacctgtct        120 ccaaataagg tcacattctc tggtactggg gattgggact tcaatgtatg agtgttttgg       180
ggcacaccag ttagcccgta acagggtagc tgcaatgatg acaggaaatc agggatgggt       240
aagcattcat aaatgtcact ctcctagagg aaagggaggc ttcctttcgg ggacattttt       300
tgtcctcatc ttgcctgggt tatagaagca actcacatag gattttttgct gggtgactcc       360 ctaccctact gcagatgatt ccactgtaca ctctgggagg gacatgtgct gtaaactcag       420
cataaaatgt catagtggtc ccaactcagc ataaaatgtc ataggcacc ccggctgggt        480 gaattcttcc agaccctgtt ttctcttcct catgcttcag acctcttcat ttcacaagca       540
gtctgttgaa gtaaccaaac tcccaggccc agagtcagcc aatctgcatt tcaacccccc       600
acctccattc ctcagcaatg gcccttcatc ttggaaatca gaattaatca cagcctctat       660
gcctgaatta aagtttgctc ttgtatcttc tttaccaagt ttacatatac tcaatattgg       720
tgtatacaac tatgtaatgc agtatgacct ctctctgtct ctgttctcct ggcaactcat       780
tcaggctcca ttcccttcat atcccacttg aatttgcact actctgcacc actgacttta       840
gaatctgtct tgtaaatagg gtcagagttc ctcagccaga tccgatggg taaaggaac         900 catgtcccca ccctgagttg agcaggtctt caagaaaccc tcttgtgagt ccactctgcc       960
ccaaagctgc ctcccaaaga tgcagcatct gtcctggcag agtgtgggca ggaaggctgc      1020
cttgccaggc tcctgactcc cagtgctgcg tggtgctgat gagctgagct gatctttgag      1080
gggccagacc aggtgaaagt tcccaccccta agcagctcag ggcagggaca gaccaaatcc     1140
aagtgcacca aatggggcca tgagaaaccc tcctgtgggg atatctgtga tctcaggaat     1200
```

```
gaccctgaga ggacactgct ctgatgctct gatgagactg agggggattc caagcttcca    1260
gggtgctggg cagtgtctcc ccagagagtg gctgttccca gtgtcaatca ggcaggaagg    1320
gtagaatgct gggacaggaa gtagcttgga ggtgggcctt aggctggtag aagttgctgc    1380
tttcttctct gtgggctcct ttctcgtgga tctggacccc aggagttccc aggcatagag    1440
aggaggggtg ccaggtgatg ggggtgatgg aggcggtggc cacggccctg agaaggctg    1500
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 9
gaggcatcag aataataaac agcagc                                          26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 10
cagcagcaac agggagccga gta                                             23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 11
ctagatactg ctgttgatgt c                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 12
ctgctctagg ttgacacact t                                               21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 13
cccatcacca tcttccagga g                                               21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer -continued

```
<400> SEQUENCE: 14
agggatgatg ttctggagag cc                                              22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 15
gtccaatcag agtgcgtcca                                                 20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 16
ggccatgctc tcagctct                                                   18

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 17
gcggcagcgg tgacta                                                     16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 18
gagcaggagc gggagc                                                     16

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 19
gaactgcggg gagagcgt                                                   18

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 20
cggagcggga gtcgga                                                     16

<210> SEQ ID NO 21
<211> LENGTH: 21
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 21
ccaaaagcac tccagatgac a                                           21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 22
aatccactac aaagctcttc                                             20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 23
ttcttctctg tgggctcct                                              19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 24
ctttctcgtg gatctggac                                              19

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 25
tcttgggtct cataatttgt tgcaggc                                     27

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 26
ttcccgcaca gccccagcag caacag                                      26

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 27

-continued

```
tgaggtacct tcagtgcctc tttcagt                                              27

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 28
cttgaagctt gtgggatct gcctcagtca                                            30

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 29
tgaggtacct atcctgagaa ctcactcact a                                         31

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 30
tgaggtacct ttgtagcttg tgcatccat                                            29

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 31
tgaggtacca cagagcggga agaccaa                                              27

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 32
ctaggtacct gcacactaag gatccaaat                                            29

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 33
agtaagctta cccttctgtt gcctaatc                                             28

<210> SEQ ID NO 34
<211> LENGTH: 27
<212> TYPE: DNA
<213> ORGANISM: Artificial Sequence
```

```
<220> FEATURE:
<223> OTHER INFORMATION: Description of Artificial Sequence:  primer

<400> SEQUENCE: 34
tgaggtacca cagagcggga agaccaa                                              27

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 35
agtaagctta cccttctgtt gcctaatc                                             28

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:  primer

<400> SEQUENCE: 36
actggtaccg gtccaatcag agtgcgt                                              27

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:  primer

<400> SEQUENCE: 37
atgaagcttc ccttagctcg ccaga                                                25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence:  primer

<400> SEQUENCE: 38
actggtaccg gcggcagcgg tgacta                                               26

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:  primer

<400> SEQUENCE: 39
actaagcttg cacactcacc tccgact                                              27

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence:  primer

<400> SEQUENCE: 40
actggtaccg acagacccca gatagcct                                             28
```

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 41
actaagctta gcctgggtga cagagact                                28

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 42
actggtaccg catgtctgtc tctgtgtcc                               29

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 43
actaagctta ctgacaactg cccactgc                                28

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 44
ccgcggtgag ta                                                 12

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: splice
      acceptor

<400> SEQUENCE: 45
ctgccaggga tg                                                 12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 46
gcacggtgag ta                                                 12

<210> SEQ ID NO 47
<211> LENGTH: 12
<212> TYPE: DNA

```
<213> ORGANISM: Artificial Sequence
<220> FEATURE:
<223> OTHER INFORMATION: Description of Artificial Sequence:
      splice donor

<400> SEQUENCE: 47
cggaggtgag tg                                                           12

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 48
tgaaggtgat tg                                                           12

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence:  splice
      acceptor <400> SEQUENCE: 49
acttcagagg ga                                                           12

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 50
ctgcggtgag ca                                                           12

<210> SEQ ID NO 51
<211> LENGTH: 12
<212> TYPE: DNA
<213> ORGANISM: Artificial Sequence
<220> FEATURE:
<223> OTHER INFORMATION: Description of Artificial Sequence:  splice
      acceptor

<400> SEQUENCE: 51
ctgagaggga gg                                                           12

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 52
agatagtaag tg                                                           12

<210> SEQ ID NO 53
<211> LENGTH: 12
<212> TYPE: DNA
<213> ORGANISM: Artificial Sequence
<220> FEATURE:
```

```
<223> OTHER INFORMATION: Description of Artificial Sequence:  splice
      acceptor

<400> SEQUENCE: 53
ctgccaggga tg                                                            12

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 54
gccaggtgat gg                                                            12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence:  splice
      acceptor

<400> SEQUENCE: 55
gccacagtgg ag                                                            12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 56
aacaggtgtc aa                                                            12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence:    splice
      acceptor

<400> SEQUENCE: 57
tcaacagtgc ca                                                            12

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 58
gtcaggtgag tc                                                            12

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence:  splice
```

-continued

```
      acceptor

<400> SEQUENCE: 59
ttcatagttc tg                                                         12

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence:
      splice donor

<400> SEQUENCE: 60
acaaggtgag ag                                                         12
```